(12) United States Patent
Buesing et al.

(10) Patent No.: US 9,796,684 B2
(45) Date of Patent: Oct. 24, 2017

(54) MATERIALS FOR ORGANIC ELECTROLUMINESCENCE DEVICES

(75) Inventors: Arne Buesing, Frankfurt am Main (DE); Holger Heil, Frankfurt am Main (DE); Teresa Mujica-Fernaud, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 902 days.

(21) Appl. No.: 13/638,975

(22) PCT Filed: Mar. 9, 2011

(86) PCT No.: PCT/EP2011/001143
§ 371 (c)(1),
(2), (4) Date: Oct. 2, 2012

(87) PCT Pub. No.: WO2011/120626
PCT Pub. Date: Oct. 6, 2011

(65) Prior Publication Data
US 2013/0032764 A1 Feb. 7, 2013

(30) Foreign Application Priority Data

Apr. 3, 2010 (DE) .................. 10 2010 013 806

(51) Int. Cl.
| | | |
|---|---|---|
| *C07D 239/26* | (2006.01) | |
| *C07D 403/04* | (2006.01) | |
| *C07D 401/04* | (2006.01) | |
| *C07D 401/10* | (2006.01) | |
| *C07D 401/14* | (2006.01) | |
| *C09K 11/06* | (2006.01) | |
| *H01L 51/00* | (2006.01) | |
| *H05B 33/14* | (2006.01) | |
| *H01L 51/50* | (2006.01) | |

(52) U.S. Cl.
CPC ......... *C07D 239/26* (2013.01); *C07D 401/04* (2013.01); *C07D 401/10* (2013.01); *C07D 401/14* (2013.01); *C09K 11/06* (2013.01); *H01L 51/0052* (2013.01); *H01L 51/0058* (2013.01); *H01L 51/0067* (2013.01); *H05B 33/14* (2013.01); *C09K 2211/1011* (2013.01); *C09K 2211/1044* (2013.01); *H01L 51/0054* (2013.01); *H01L 51/5048* (2013.01); *Y02E 10/549* (2013.01)

(58) Field of Classification Search
None
See application file for complete search history.

(56) References Cited

U.S. PATENT DOCUMENTS

| 8,217,570 | B2 | 7/2012 | Kawamura et al. | |
|---|---|---|---|---|
| 2006/0125380 | A1* | 6/2006 | Nagara et al. | ........... 313/504 |
| 2006/0154105 | A1 | 7/2006 | Yamamoto et al. | |
| 2008/0111473 | A1 | 5/2008 | Kawamura et al. | |
| 2013/0032764 | A1 | 2/2013 | Buesing et al. | |

FOREIGN PATENT DOCUMENTS

| EP | 1582516 A4 | 2/2008 |
|---|---|---|
| EP | 2108689 A3 | 3/2010 |
| JP | 2004002297 A | 1/2004 |
| JP | 2009-249378 A | 10/2009 |
| JP | 2010034548 A * | 2/2010 |
| JP | 2012-503314 A | 2/2012 |
| JP | 2013523788 A | 6/2013 |
| WO | WO-2010114266 A3 | 12/2010 |
| WO | WO-2011037380 A3 | 10/2011 |

OTHER PUBLICATIONS

Machine English translation of Tominaga et al. (JP 2010-034548 A). Jun. 27, 2015.*
International Search Report for PCT/EP2011/001143 mailed May 19, 2011.

* cited by examiner

*Primary Examiner* — J. L. Yang

(57) ABSTRACT

The invention relates to pyrimidine derivatives according to formula (I),

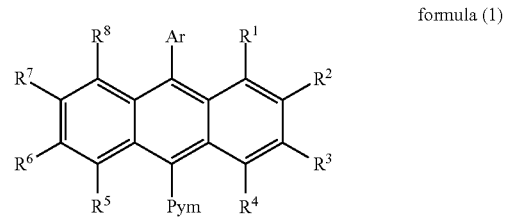

and to organic electroluminescent devices comprising said pyrimidine derivatives as electron transport material.

22 Claims, No Drawings

MATERIALS FOR ORGANIC ELECTROLUMINESCENCE DEVICES

RELATED APPLICATIONS

This application is a national stage application (under 35 U.S.C. §371) of PCT/EP2011/001143, filed Mar. 9, 2011, which claims benefit of German Patent Application No. 10 2010 013 806.1, filed Apr. 3, 2010.

The present invention relates to pyrimidine derivatives and to organic electroluminescent devices which comprise these pyrimidine derivatives as electron-transport materials.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. However, further improvements are still desirable. Thus, there is still a need for improvement, in particular, in relation to the lifetime, the efficiency and the operating voltage of organic electroluminescent devices. It is furthermore necessary for the compounds to have high thermal stability and a high glass-transition temperature and to be sublimable without decomposition.

Improvements in the properties are still also desirable, in particular, in the electron-transport materials since the properties of the electron-transport material, in particular, also exert a significant influence on the above-mentioned properties of the organic electroluminescent device. In particular, there is a need for improvement in electron-transport materials which simultaneously result in good efficiency, a long lifetime and a low operating voltage. The properties of the electron-transport material, in particular, are also frequently limiting for the lifetime, the efficiency and the operating voltage of the organic electroluminescent device.

It would be desirable here to have available electron-transport materials which result in better electron injection into the emitting layer, since an electron-richer emission layer results in better efficiency. In addition, the operating voltage can be reduced by better injection. Further improvements in the electron-transport material are therefore necessary for this purpose.

Furthermore, there is in general still a need for improvement in the processability of the materials, since many materials which are used in accordance with the prior art in organic electroluminescent devices tend to crystallise on the vapour-deposition source in the process for the production of the electroluminescent device and thus clog the vapour-deposition source. These materials can therefore only be employed with increased technical difficulty in mass production.

Electroluminescent devices which use $AlQ_3$ as electron conductor have already been known for some time and were described as long ago as 1993 in U.S. Pat. No. 4,539,507. $AlQ_3$ has since then frequently been used as electron-transport material, but has a number of disadvantages: it cannot be vapour-deposited without leaving a residue, since it partially decomposes at the sublimation temperature, which represents a major problem, in particular for production plants. This has the consequence that the vapour-deposition sources have to be repeatedly cleaned or exchanged. Furthermore, decomposition products of $AlQ_3$ enter the OLED, where they contribute to a shortened lifetime and reduced quantum and power efficiency. In addition, $AlQ_3$ has low electron mobility, which results in higher voltages and thus reduced power efficiency. In order to avoid short circuits in the display, it is desirable to increase the layer thickness; this is not possible with $AlQ_3$ owing to the low charge-carrier mobility and the resultant increase in voltage. The charge-carrier mobility of other electron conductors (U.S. Pat. No. 4,539,507) is likewise too low to build up thicker layers therewith, where the lifetime of the OLED is even worse than in the case of the use of $AlQ_3$. The inherent colour (yellow in the solid) of $AlQ_3$, which can result in colour shifts, especially in blue OLEDs, due to reabsorption and weak reemission, also proves unfavourable. Blue OLEDs can only be produced here with considerable adverse effects regarding efficiency and colour location.

Thus, there continues to be a demand for electron-transport materials which result in good efficiencies and at the same time in long lifetimes in organic electroluminescent devices. Surprisingly, it has now been found that the pyrimidine derivatives shown below exhibit significant improvements as electron-transport materials compared with the materials in accordance with the prior art. Using these materials, it is possible simultaneously to obtain high efficiencies and long lifetimes, which was not possible to this extent using materials in accordance with the prior art. Moreover, it has been found that, in addition, the operating voltage can be reduced significantly, which results in higher power efficiencies.

It has furthermore been found that organic electroluminescent devices which comprise these pyrimidine derivatives as electron-transport material in combination with an organic alkali-metal compound exhibit significant improvements compared with the prior art. Using this material combination, high efficiencies and long lifetimes are achieved at the same time, and the operating voltages are reduced.

EP 1582516 and WO 2006/067931 disclose the use of nitrogen-containing heterocycles as electron-transport material in organic electroluminescent devices. However, there is also still a further need for improvement compared with the materials disclosed therein, in particular with respect to operating voltage, lifetime and efficiency.

The invention thus relates to a compound of the formula (1),

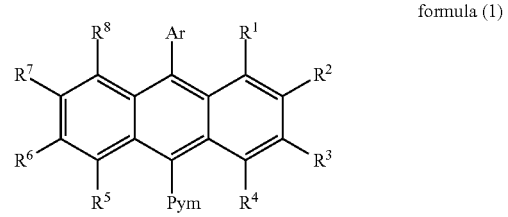

formula (1)

where the following applies to the symbols and indices used:

Pym is a group of the following formula (2) or (3):

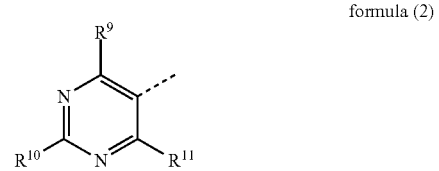

formula (2)

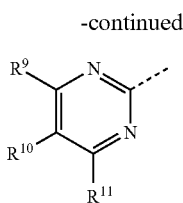

formula (3)

where the dashed bond indicates the bond to the anthracene;

Ar is a condensed aryl or heteroaryl group having 10 to 30 aromatic ring atoms, which may be substituted by one or more radicals $R^{12}$;

$R^1, R^2, R^3, R^4, R^5, R^6, R^7, R^8, R^9, R^{10}, R^{11}, R^{12}$ are on each occurrence, identically or differently, H, D, F, Cl, Br, I, CHO, $N(R^{13})_2$, $N(Ar^1)_2$, $B(Ar^1)_2$, $Si(R^{13})_2$, $Si(Ar^1)_2$, $C(=O)Ar^1$, $P(=O)(Ar^1)_2$, $S(=O)Ar^1$, $S(=O)_2Ar^1$, $CR^{13}=CR^{13}Ar^1$, CN, $NO_2$, $Si(R^{13})_3$, $B(OR^{13})_2$, $B(R^{13})_2$, $B(N(R^{13})_2)_2$, $OSO_2R^{13}$, a straight-chain alkyl, alkenyl, alkynyl, alkoxy or thioalkoxy group having 1 to 40 C atoms or a branched or cyclic alkyl, alkenyl, alkynyl, alkoxy or thioalkoxy group having 3 to 40 C atoms, each of which may be substituted by one or more radicals $R^{13}$, where one or more non-adjacent $CH_2$ groups may be replaced by $R^{13}C=CR^{13}$, $C\equiv C$, $Si(R^{13})_2$, $Ge(R^{13})_2$, $Sn(R^{13})_2$, $C=O$, $C=S$, $C=Se$, $C=NR^{13}$, $P(=O)(R^{13})$, SO, $SO_2$, $NR^{13}$, O, S or $CONR^{13}$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^{13}$, or an aryloxy or heteroaryloxy group having 5 to 60 aromatic ring atoms, which may be substituted by one or more radicals $R^{13}$, or a combination of these systems; two or more adjacent substituents $R^1$ to $R^{12}$ here may also form a mono- or polycyclic, aliphatic or aromatic ring system with one another;

$Ar^1$ is on each occurrence, identically or differently, an aromatic or heteroaromatic ring system having 5 to 30 aromatic ring atoms, which may be substituted by one or more radicals $R^{13}$; two radicals $Ar^1$ here which are bonded to the same nitrogen, phosphorus, silicon or boron atom may also be linked to one another by a single bond or a bridge selected from $B(R^{13})$, $C(R^{13})_2$, $Si(R^{13})_2$, $C=O$, $C=NR^{13}$, $C=C(R^{13})_2$, O, S, $S=O$, $SO_2$, $N(R^{13})$, $P(R^{13})$ and $P(=O)R^{13}$;

$R^{13}$ is on each occurrence, identically or differently, H, D or an aliphatic, aromatic and/or heteroaromatic hydrocarbon radical having 1 to 20 C atoms, in which, in addition, H atoms may be replaced by D or F; two or more adjacent substituents $R^{13}$ here may also form a mono- or polycyclic, aliphatic or aromatic ring system with one another.

Adjacent substituents $R^1$ to $R^{12}$ in the sense of this invention are taken to mean substituents which are bonded to directly adjacent carbon atoms, i.e. to carbon atoms which are bonded to one another.

An aryl group in the sense of this invention contains at least 6 C atoms; a heteroaryl group in the sense of this invention contains at least 2 C atoms and at least 1 heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group.

A condensed aryl or heteroaryl group in the sense of this invention is taken to mean an aryl or heteroaryl group in which at least two aromatic or heteroaromatic rings, for example benzene rings, are fused to one another, i.e. are condensed onto one another by anellation, i.e. have at least one common edge and thus also a common aromatic system. Thus, for example, systems such as naphthalene, anthracene, phenanthrene, benzanthracene, pyrene, etc., are to be regarded as condensed aryl groups and quinoline, acridine, benzothiophene, carbazole, etc., are to be regarded as condensed heteroaryl groups in the sense of this invention, while, for example, fluorene, spirobifluorene, etc. are not condensed aryl groups since separate aromatic electron systems are involved here.

An aromatic ring system in the sense of this invention contains at least 6 C atoms in the ring system. A heteroaromatic ring system in the sense of this invention contains at least 1 C atom and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which a plurality of aryl or heteroaryl groups may also be interrupted by a short non-aromatic unit (preferably less than 10% of the atoms other than H), such as, for example, an $sp^3$-hybridised C, N or O atom. Thus, for example, systems such as 9,9'-spirobifluorene, 9,9-diarylfluorene, triarylamine, diaryl ether, stilbene, benzophenone, etc., are also intended to be taken to be aromatic ring systems in the sense of this invention. Likewise, an aromatic or heteroaromatic ring system is taken to mean systems in which a plurality of aryl or heteroaryl groups are linked to one another by single bonds, for example biphenyl, terphenyl or bipyridine.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, tert-pentyl, 2-pentyl, neopentyl, cyclopentyl, n-hexyl, s-hexyl, tert-hexyl, 2-hexyl, 3-hexyl, neohexyl, cyclohexyl, 2-methylpentyl, n-heptyl, 2-heptyl, 3-heptyl, 4-heptyl, cycloheptyl, 1-methylcycloheptyl, n-octyl, 2-ethylhexyl, cyclooctyl, 1-bicyclo[2.2.2]octyl, 2-bicyclo-[2.2.2]octyl, 2-(2,6-dimethyl)octyl, 3-(3,7-dimethyl)octyl, trifluoromethyl, pentafluoroethyl and 2,2,2-trifluoroethyl. An alkenyl group is particularly preferably taken to mean the radicals ethenyl, propenyl, butenyl, pentenyl, cyclopentenyl, hexenyl, cyclohexenyl, heptenyl, cycloheptenyl, octenyl and cyclooctenyl. An alkynyl group is particularly preferably taken to mean the radicals ethynyl, propynyl, butynyl, pentynyl, hexynyl, heptynyl or octynyl. A $C_1$- to $C_{40}$-alkoxy group is particularly preferably taken to mean methoxy, trifluromethyoxy, ethoxy, n-propoxy, i-propoxy, n-butoxy, i-butoxy, s-butoxy, t-butoxy or 2-methylbutoxy. An aromatic or heteroaromatic ring system having 5-60 aromatic ring atoms, which may in each case also be substituted by the above-mentioned radicals R and which may be linked to the aromatic or heteroaromatic ring system via any desired positions, is taken to mean, in particular, groups derived from benzene, naphthalene, anthracene, phenanthrene, benzanthracene, pyrene, chrysene, perylene, fluoranthene, benzofluoranthene, naphthacene, pentacene, benzopyrene, biphenyl, biphenylene, terphenyl, terphenylene, fluorene, benzofluorene, dibenzofluorene, spirobifluorene, dihydrophenanthrene, dihydropyrene, tetrahydropyrene, cis- or trans-indenofluorene, cis- or trans-monobenzo-indenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridoimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

The compounds of the formula (1) preferably have a glass-transition temperature $T_G$ of greater than 70° C., particularly preferably greater than 90° C., very particularly preferably greater than 110° C.

In a preferred embodiment of the invention, the group of the formula (2) is selected from the groups of the formula (2a), and the group of the formula (3) is selected from the groups of the formulae (3a) and (3b),

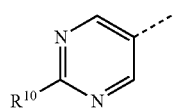

formula (2a)

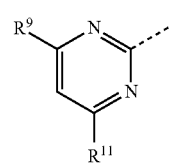

formula (3a)

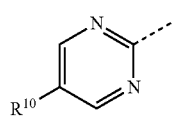

formula (3b)

where the symbols used have the meanings indicated above.

Preference is thus given to the compounds of the following formulae (4), (5) and (6),

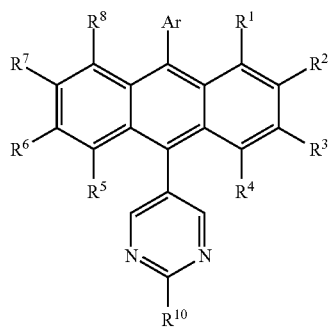

formula (4)

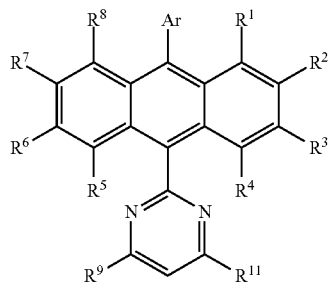

formula (5)

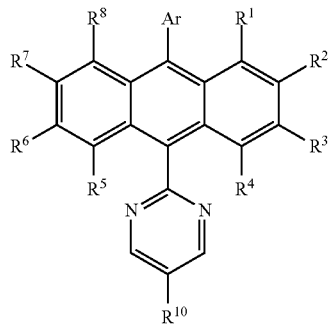

formula (6)

where the symbols used have the meanings indicated above.

Particular preference is given to the compounds of the following formulae (4a), (5a) and (6a),

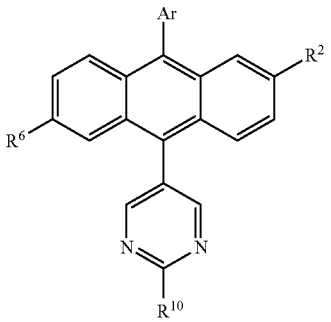

formula (4a)

formula (5a)

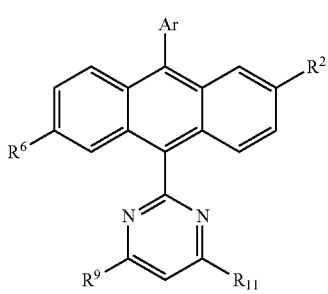

formula (6a)

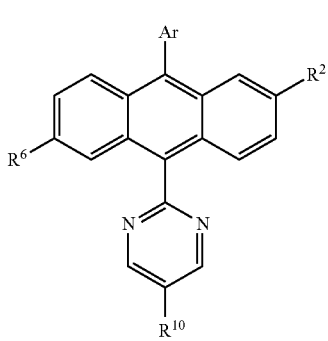

where the symbols used have the meanings indicated above.

In a preferred embodiment of the invention, the group Ar in the compounds of the formulae (1), (4) to (6) and (4a) to (6a) stands for a condensed aryl or heteroaryl group having 10 to 20 aromatic ring atoms, which may in each case be substituted by one or more radicals $R^{12}$, particularly preferably for a condensed aryl group having 10 to 16 C atoms, which may be substituted by one or more radicals $R^{12}$, very particularly preferably for naphthalene, anthracene, phenanthrene, benzanthracene, chrysene, benzophenanthrene or pyrene, each of which may be substituted by one or more radicals $R^{12}$.

Preferred groups Ar are selected from the structures of the following formulae (7) to (27):

formula (7)

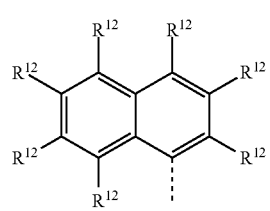

formula (8)

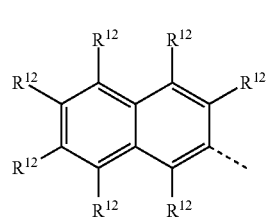

formula (9)

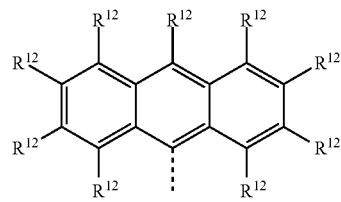

formula (10)

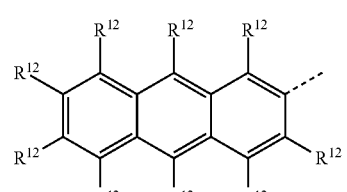

formula (11)

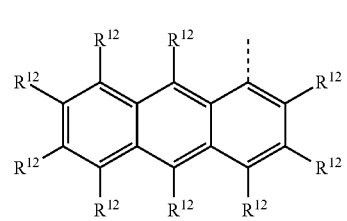

formula (12)

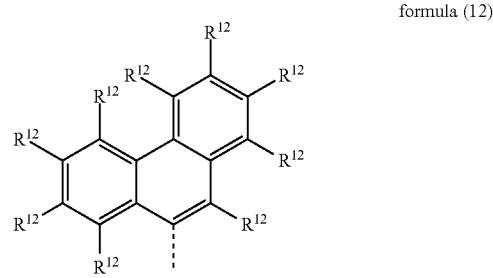

formula (13)

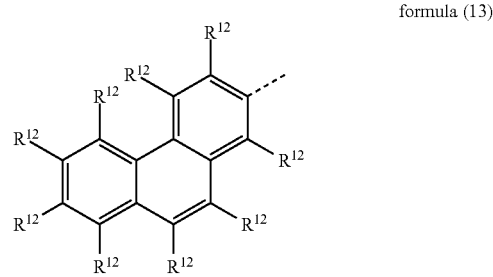

formula (14)

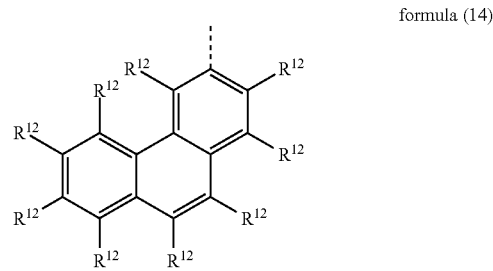

formula (15)
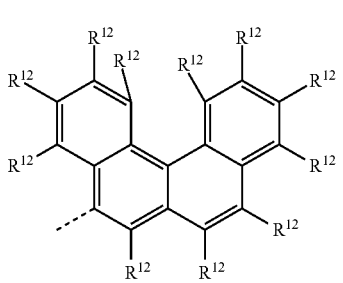
formula (16)
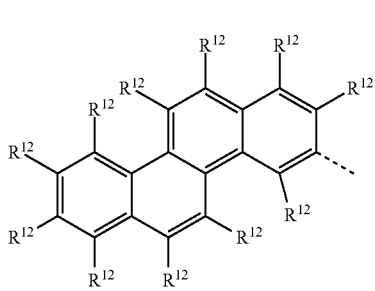
formula (17)
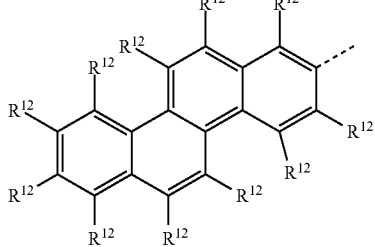
formula (18)
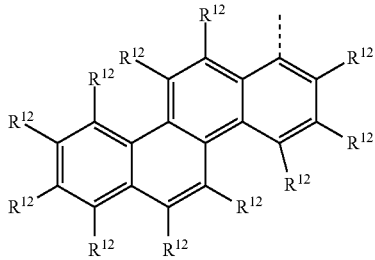
formula (19)
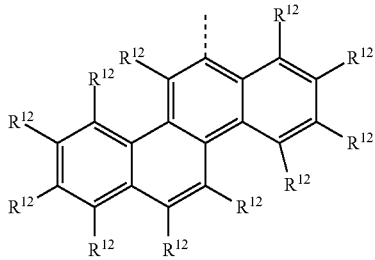
formula (20)
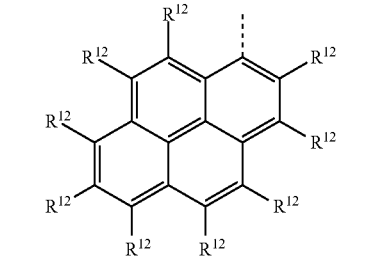
formula (21)
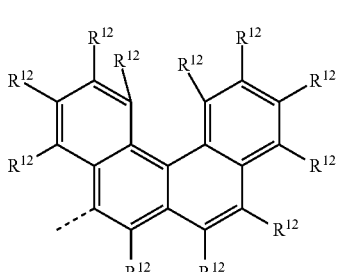
formula (22)
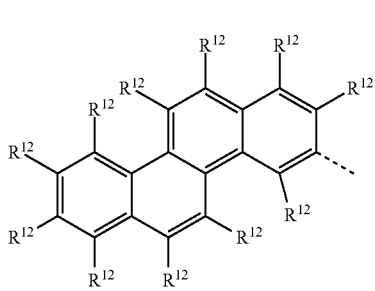
formula (23)
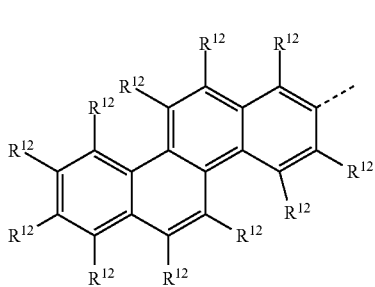
formula (24)
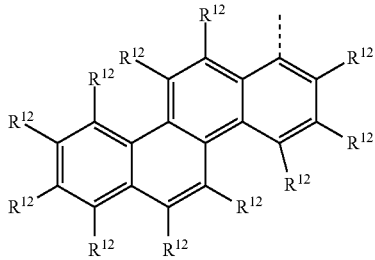
formula (25)
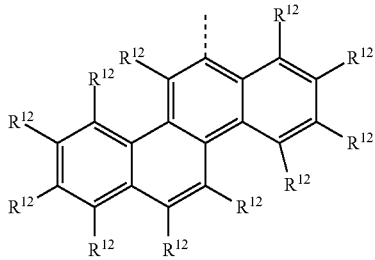
formula (26)
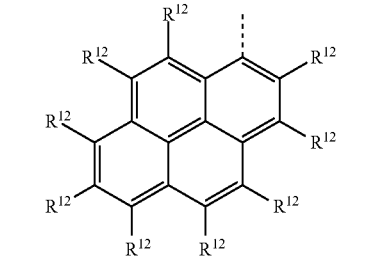

formula (27)

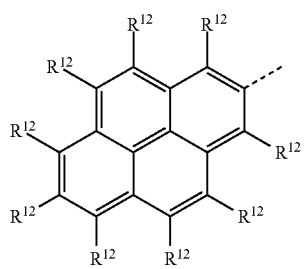

where the symbols used have the meanings indicated above, and the dashed bond in each case represents the position of the link to the anthracene.

Of the groups mentioned above, particular preference is given to the groups of the formulae (7), (8), (9), (10), (12), (14), (16) and (26).

Particularly preferred groups Ar are the groups of the following formulae (7a), (8a), (9a), (10a), (12a), (14a), (16a) and (26a):

formula (7a)

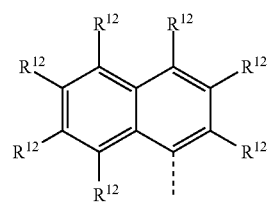

formula (8a)

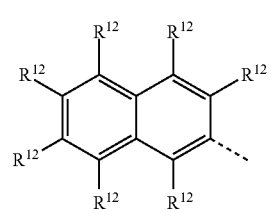

formula (9a)

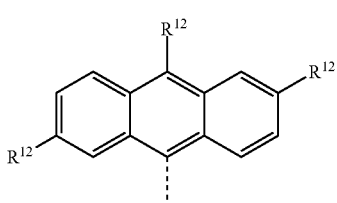

formula (10a)

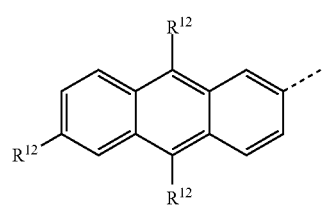

formula (12a)

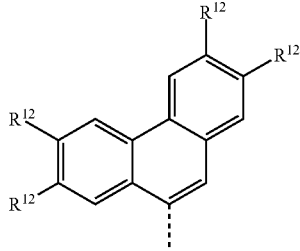

formula (14a)

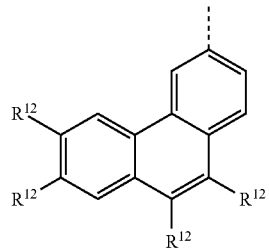

formula (16a)

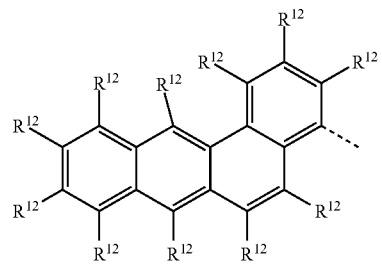

formula (26a)

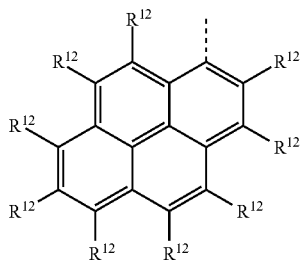

where the symbols used have the meanings indicated above.

In a preferred embodiment of the invention, the radicals $R^1$ to $R^{12}$ are selected on each occurrence, identically or differently, from the group consisting of H, D, F, $N(Ar^1)_2$, $C(=O)Ar^1$, $P(=O)(Ar^1)_2$, $S(=O)Ar^1$, $S(=O)_2Ar^1$, CN, $Si(R^{13})_3$, a straight-chain alkyl group having 1 to 10 C atoms or a branched or cyclic alkyl group having 3 to 10 C atoms, each of which may be substituted by one or more radicals $R^{13}$, where one or more non-adjacent $CH_2$ groups may be replaced by $R^{13}C=CR^{13}$ and where one or more H atoms may be replaced by D or F, or an aromatic or heteroaromatic ring system having 5 to 30 aromatic ring atoms, which may in each case be substituted by one or more radicals $R^{13}$; two or more adjacent substituents $R^1$ to $R^{12}$ here may also form a mono- or polycyclic, aliphatic or aromatic ring system with one another.

In a particularly preferred embodiment of the invention, the radicals $R^1$ to $R^{12}$ are selected on each occurrence, identically or differently, from the group consisting of H, D, F, CN, a straight-chain alkyl group having 1 to 8 C atoms or a branched or cyclic alkyl group having 3 to 8 C atoms, each of which may be substituted by one or more radicals R$^{13}$ and where one or more H atoms may be replaced by D, or an aromatic or heteroaromatic ring system having 5 to 24 aromatic ring atoms, which may in each case be substituted by one or more radicals R$^{13}$.

This preference also applies, in particular, to the radicals R$^2$ and R$^6$ in the structures of the formulae (4a) to (6a).

The radicals R$^9$, R$^{10}$ and R$^{11}$ particularly preferably stand, identically or differently, for H or an aromatic or heteroaromatic ring system having 5 to 24 aromatic ring atoms, which may in each case be substituted by one or more radicals R$^{13}$. If the R$^9$, R$^{10}$ and/or R$^{11}$ stand for an aromatic or heteroaromatic ring system, they preferably stand for phenyl, o-, m- or p-biphenyl, o-, m- or p-terphenyl, branched terphenyl or linear or branched quaterphenyl, each of which may be substituted by one or more radicals R$^{13}$, but is preferably unsubstituted.

Examples of preferred compounds according to the invention are compounds 1 to 70 depicted below.

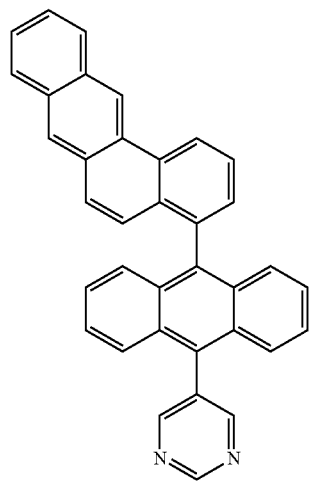 [SMILES: c1ccc2cc3c(ccc4c(-c5c6ccccc6c(-c6cncnc6)c6ccccc56)cccc43)cc2c1]

1

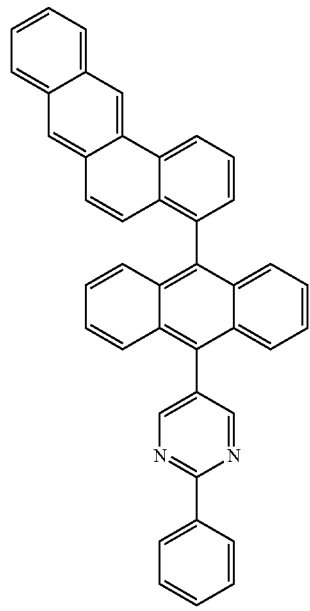 [SMILES: c1ccc(-c2ncc(-c3c4ccccc4c(-c4cccc5c4ccc4cc6ccccc6cc45)c4ccccc34)cn2)cc1]

2

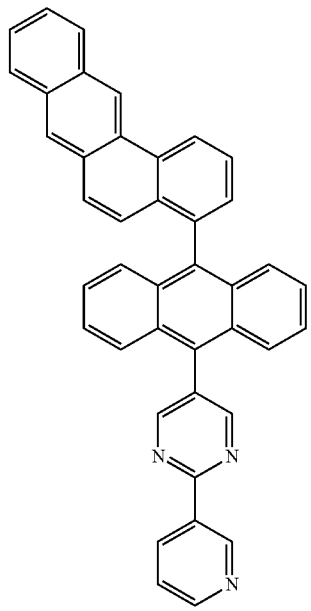 [SMILES: c1cncc(-c2ncc(-c3c4ccccc4c(-c4cccc5c4ccc4cc6ccccc6cc45)c4ccccc34)cn2)c1]

3

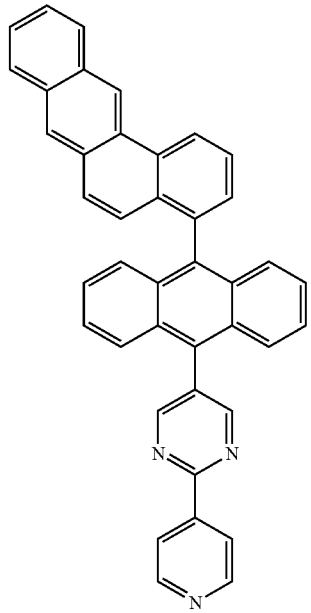 [SMILES: c1ccc2cc3c(ccc4c(-c5c6ccccc6c(-c6cnc(-c7ccncc7)nc6)c6ccccc56)cccc43)cc2c1]

4

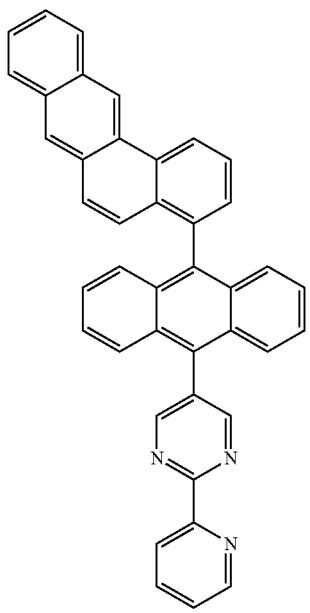 [SMILES: c1ccc(-c2ncc(-c3c4ccccc4c(-c4cccc5c4ccc4cc6ccccc6cc45)c4ccccc34)cn2)nc1]
5
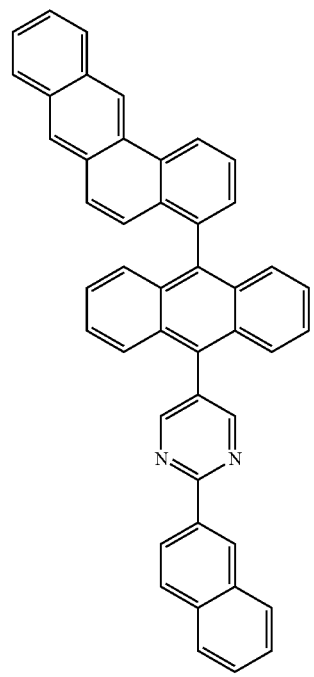
7
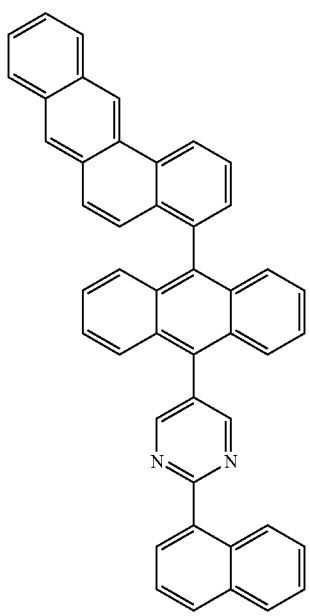 [SMILES: c1ccc2cc3c(ccc4c(-c5c6ccccc6c(-c6cnc(-c7cccc8ccccc78)nc6)c6ccccc56)cccc43)cc2c1]
6
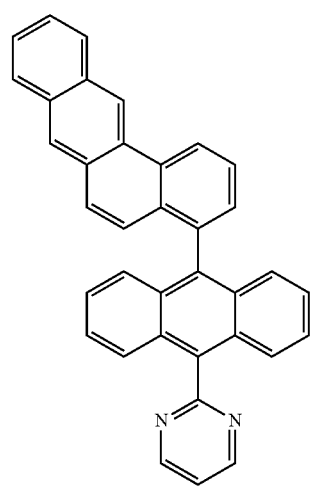 [SMILES: c1cnc(-c2c3ccccc3c(-c3cccc4c3ccc3cc5ccccc5cc34)c3ccccc23)nc1]
8

-continued
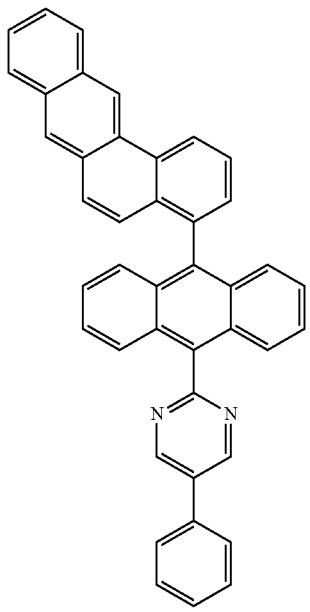 [SMILES: c1ccc(-c2cnc(-c3c4ccccc4c(-c4cccc5c4ccc4cc6ccccc6cc45)c4ccccc34)nc2)cc1]
9
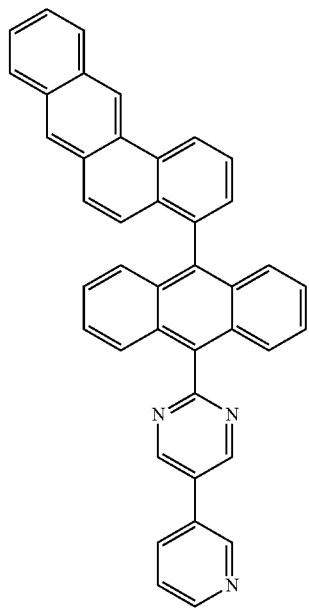 [SMILES: c1cncc(-c2cnc(-c3c4ccccc4c(-c4cccc5c4ccc4cc6ccccc6cc45)c4ccccc34)nc2)c1]
11
10
12

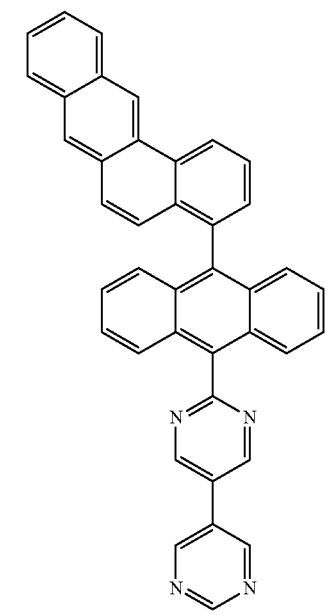 [SMILES: c1ccc2cc3c(ccc4c(-c5c6ccccc6c(-c6ncc(-c7cncnc7)cn6)c6ccccc56)cccc43)cc2c1]
13
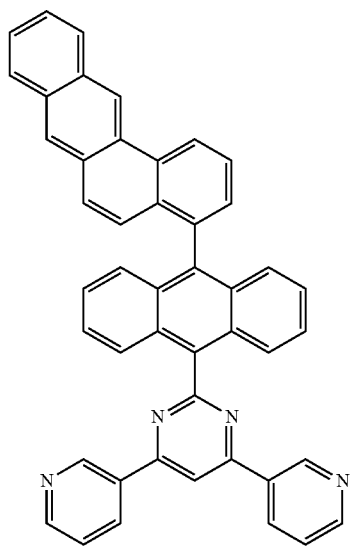
15
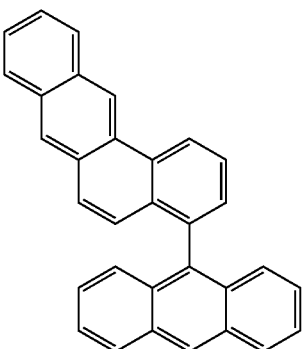
16
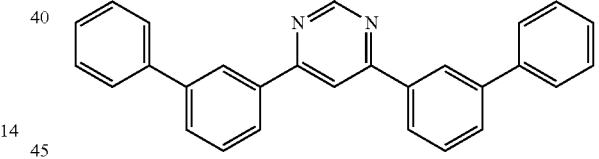
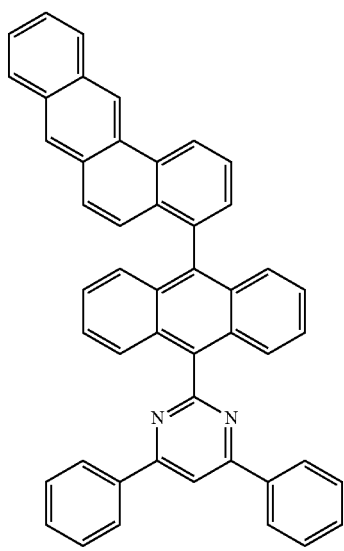 [SMILES: c1ccc(-c2cc(-c3ccccc3)nc(-c3c4ccccc4c(-c4cccc5c4ccc4cc6ccccc6cc45)c4ccccc34)n2)cc1]
14
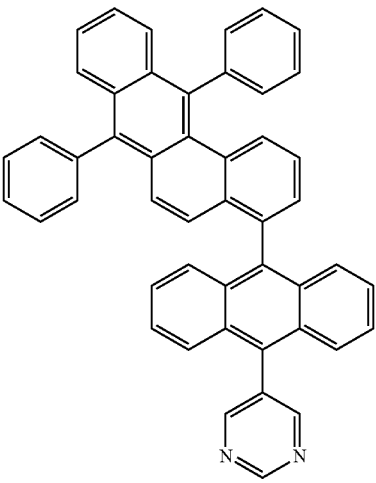 [SMILES: c1ccc(-c2c3ccccc3c(-c3ccccc3)c3c2ccc2c(-c4c5ccccc5c(-c5cncnc5)c5ccccc45)cccc23)cc1]
17

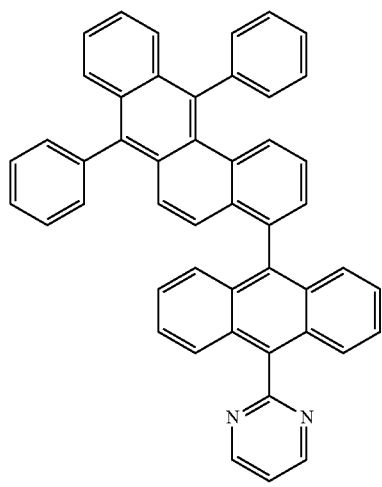 [SMILES: c1ccc(-c2c3ccccc3c(-c3ccccc3)c3c2ccc2c(-c4c5ccccc5c(-c5ncccn5)c5ccccc45)cccc23)cc1]
18
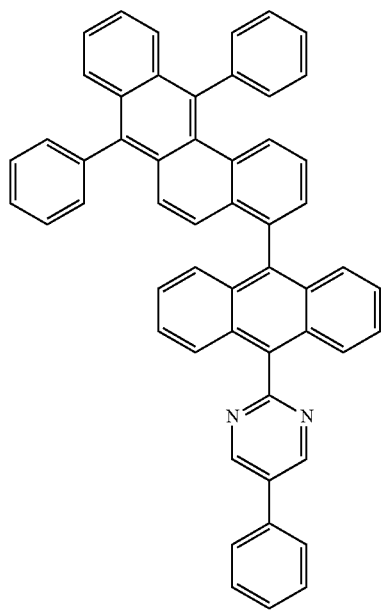 [SMILES: c1ccc(-c2cnc(-c3c4ccccc4c(-c4cccc5c4ccc4c(-c6ccccc6)c6ccccc6c(-c6ccccc6)c45)c4ccccc34)nc2)cc1]
19
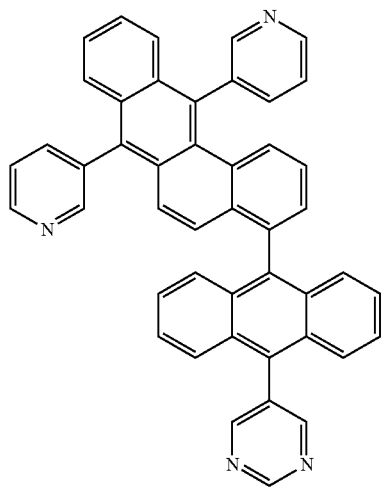 [SMILES: c1cncc(-c2c3ccccc3c(-c3cccnc3)c3c2ccc2c(-c4c5ccccc5c(-c5cncnc5)c5ccccc45)cccc23)c1]
20
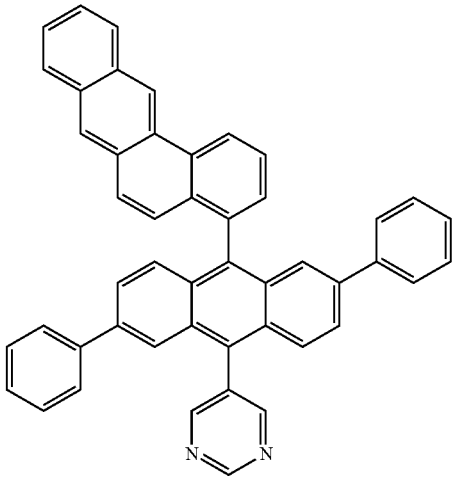 [SMILES: c1ccc(-c2ccc3c(-c4cccc5c4ccc4cc6ccccc6cc45)c4cc(-c5ccccc5)ccc4c(-c4cncnc4)c3c2)cc1]
21
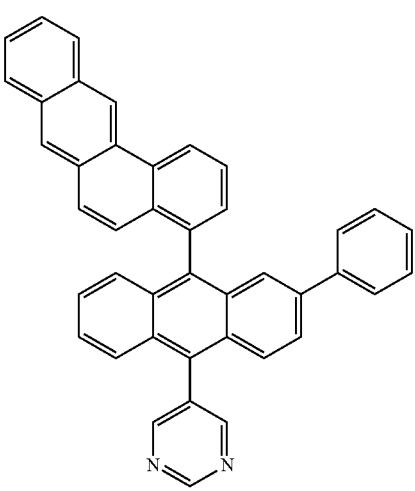 [SMILES: c1ccc(-c2ccc3c(-c4cncnc4)c4ccccc4c(-c4cccc5c4ccc4cc6ccccc6cc45)c3c2)cc1]
22
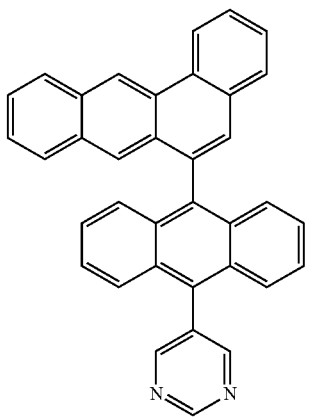 [SMILES: c1ccc2cc3c(cc2c1)c(-c1c2ccccc2c(-c2cncnc2)c2ccccc12)cc1ccccc13]
23

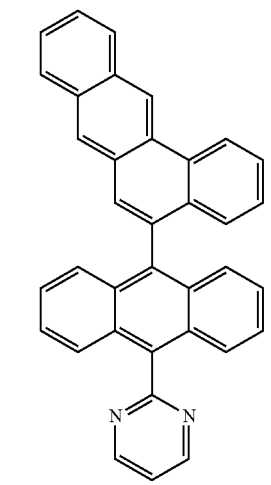 [SMILES: c1cnc(-c2c3ccccc3c(-c3cc4cc5ccccc5cc4c4ccccc34)c3ccccc23)nc1]
24
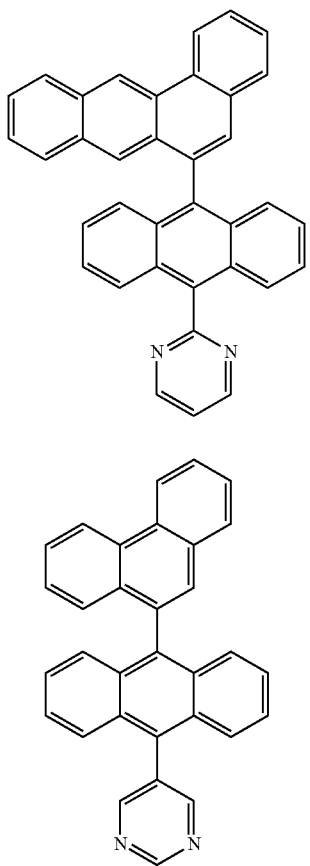
25
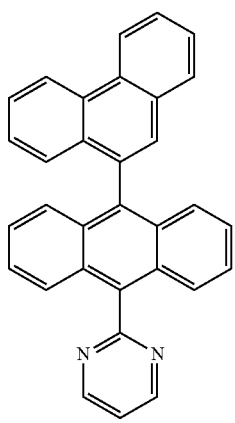 [SMILES: c1cnc(-c2c3ccccc3c(-c3cc4ccccc4c4ccccc34)c3ccccc23)nc1]
27
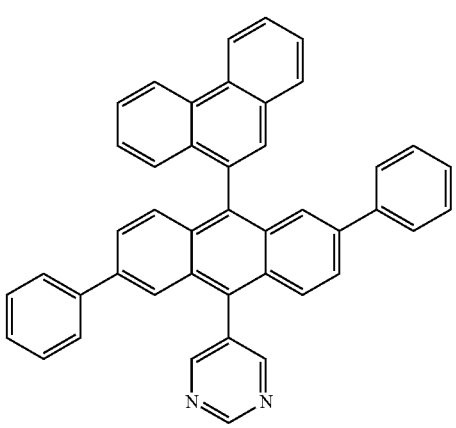 [SMILES: c1ccc(-c2ccc3c(-c4cc5ccccc5c5ccccc45)c4cc(-c5ccccc5)ccc4c(-c4cncnc4)c3c2)cc1]
28
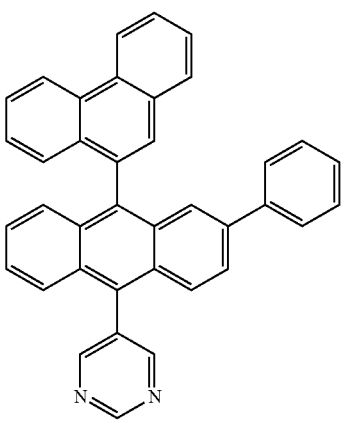 [SMILES: c1ccc(-c2ccc3c(-c4cncnc4)c4ccccc4c(-c4cc5ccccc5c5ccccc45)c3c2)cc1]
29

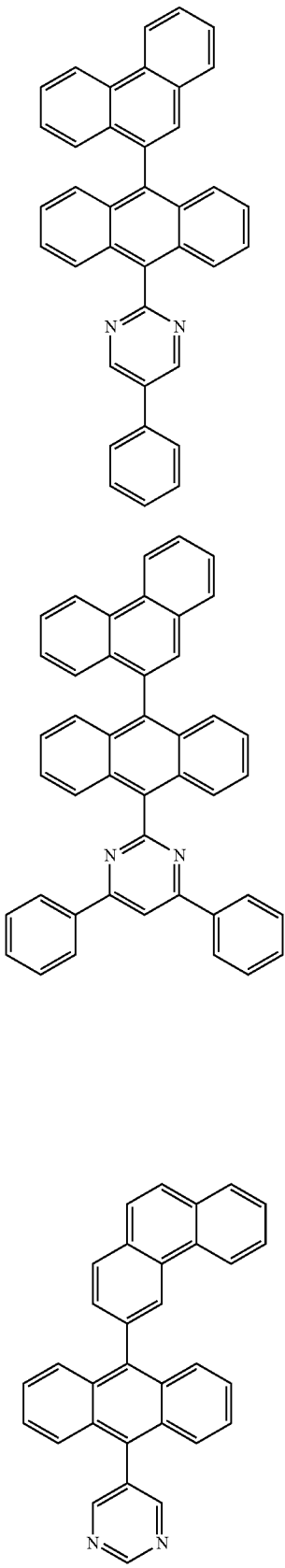
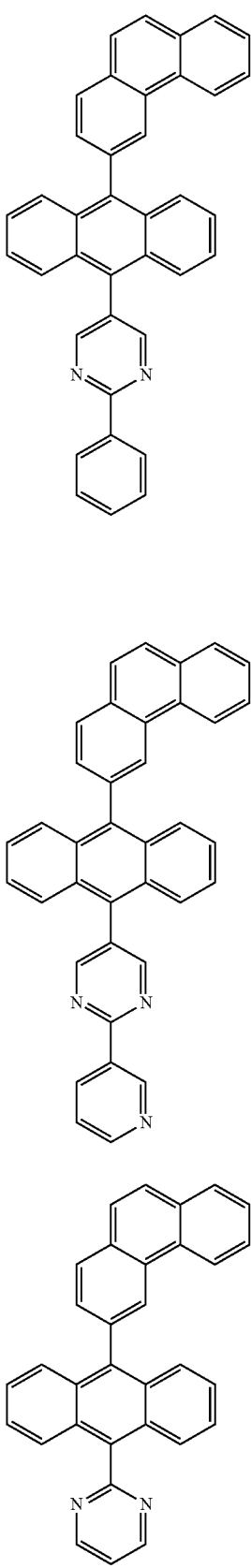

36
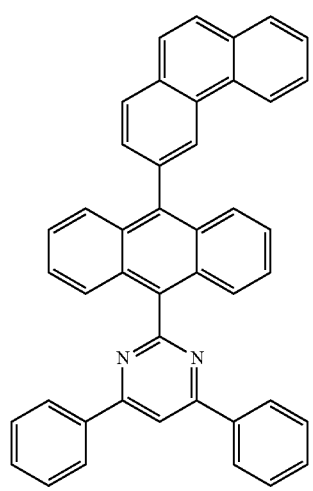 [SMILES: c1ccc(-c2cc(-c3ccccc3)nc(-c3c4ccccc4c(-c4ccc5ccc6ccccc6c5c4)c4ccccc34)n2)cc1]
37
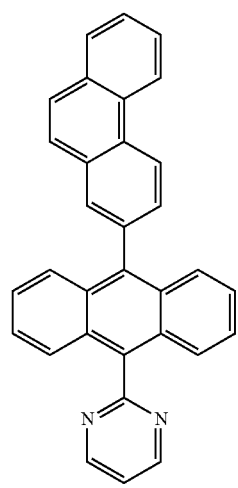 [SMILES: c1cnc(-c2c3ccccc3c(-c3ccc4c(ccc5ccccc54)c3)c3ccccc23)nc1]
38
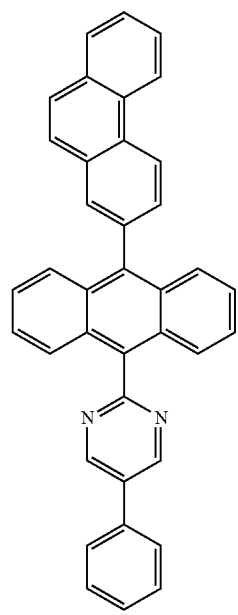 [SMILES: c1ccc(-c2cnc(-c3c4ccccc4c(-c4ccc5c(ccc6ccccc65)c4)c4ccccc34)nc2)cc1]
39
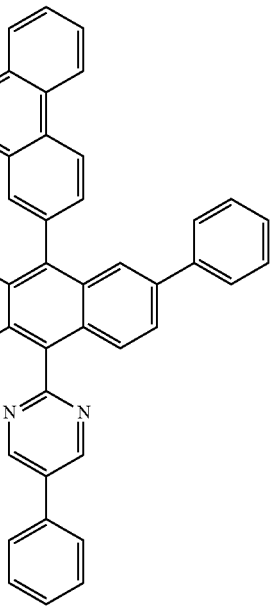
40
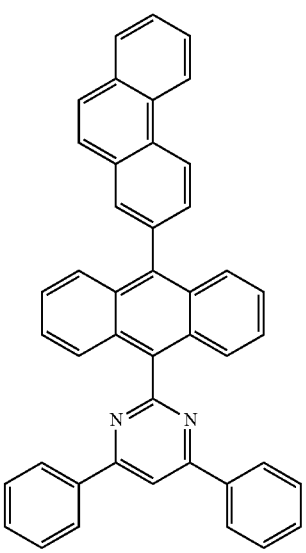 [SMILES: c1ccc(-c2cc(-c3ccccc3)nc(-c3c4ccccc4c(-c4ccc5c(ccc6ccccc65)c4)c4ccccc34)n2)cc1]
41
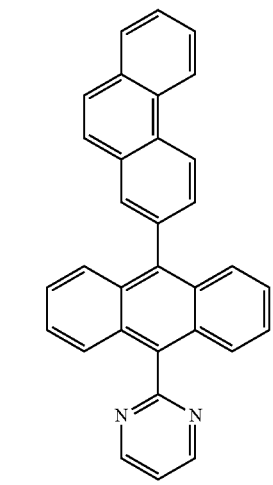 [SMILES: c1cnc(-c2c3ccccc3c(-c3ccc4c(ccc5ccccc54)c3)c3ccccc23)nc1]

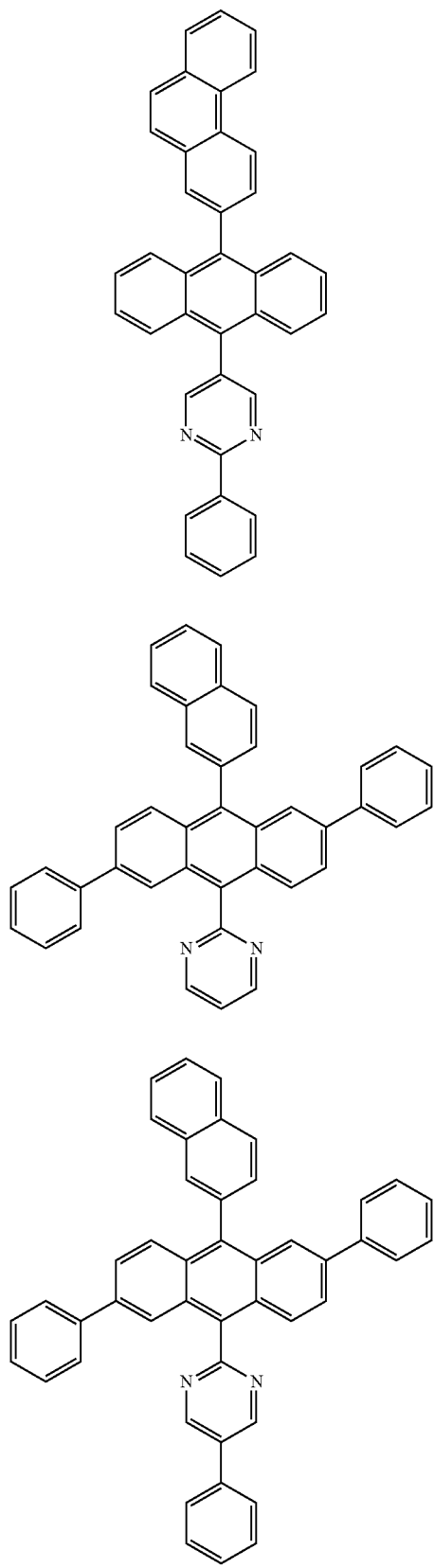
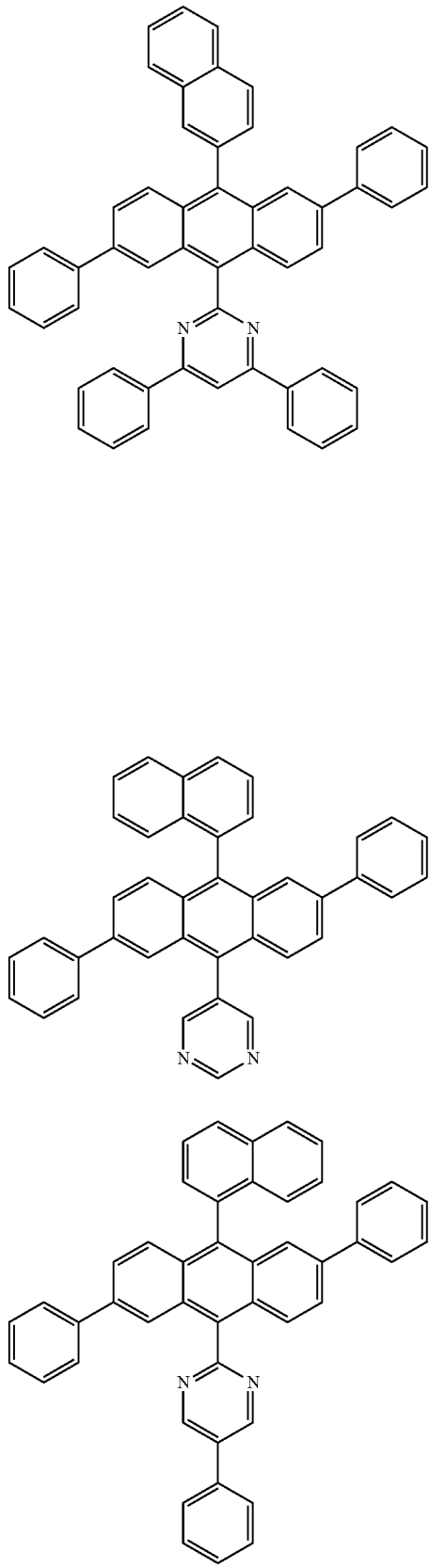

-continued
48
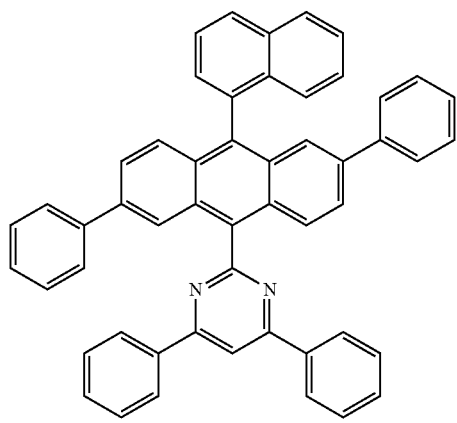 [SMILES: c1ccc(-c2ccc3c(-c4cccc5ccccc45)c4cc(-c5ccccc5)ccc4c(-c4nc(-c5ccccc5)cc(-c5ccccc5)n4)c3c2)cc1]
49
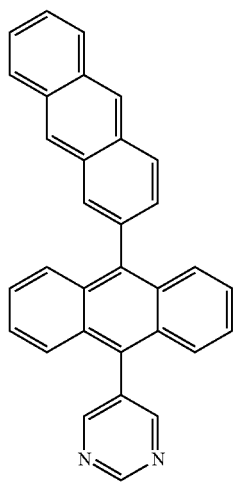 [SMILES: c1ccc2cc3cc(-c4c5ccccc5c(-c5cncnc5)c5ccccc45)ccc3cc2c1]
50
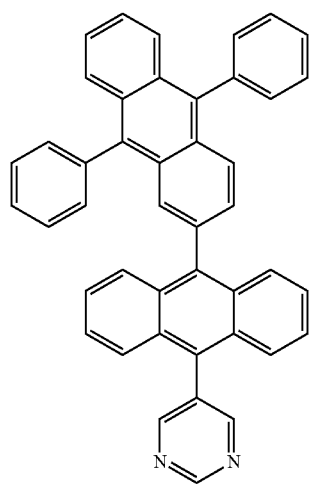 [SMILES: c1ccc(-c2c3ccccc3c(-c3ccccc3)c3cc(-c4c5ccccc5c(-c5cncnc5)c5ccccc45)ccc23)cc1]
-continued
51
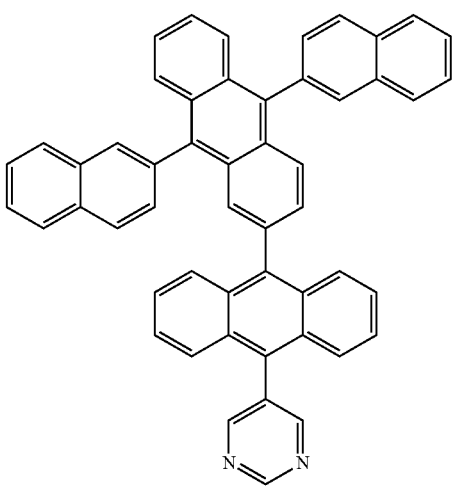 [SMILES: c1ccc2cc(-c3c4ccccc4c(-c4ccc5ccccc5c4)c4cc(-c5c6ccccc6c(-c6cncnc6)c6ccccc56)ccc34)ccc2c1]
52
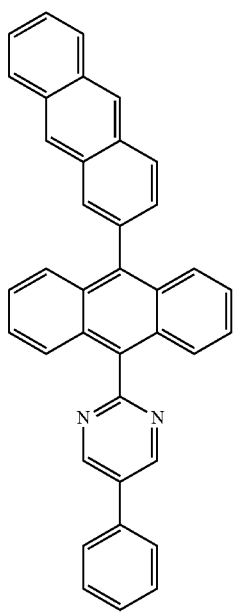 [SMILES: c1ccc(-c2cnc(-c3c4ccccc4c(-c4ccc5cc6ccccc6cc5c4)c4ccccc34)nc2)cc1]
53
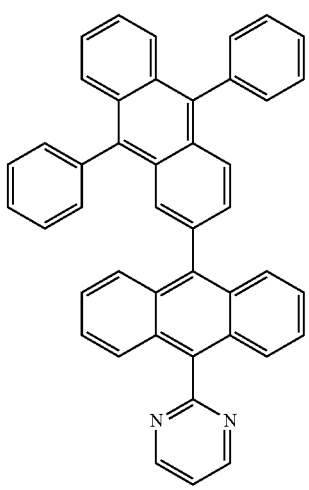 [SMILES: c1ccc(-c2c3ccccc3c(-c3ccccc3)c3cc(-c4c5ccccc5c(-c5ncccn5)c5ccccc45)ccc23)cc1]

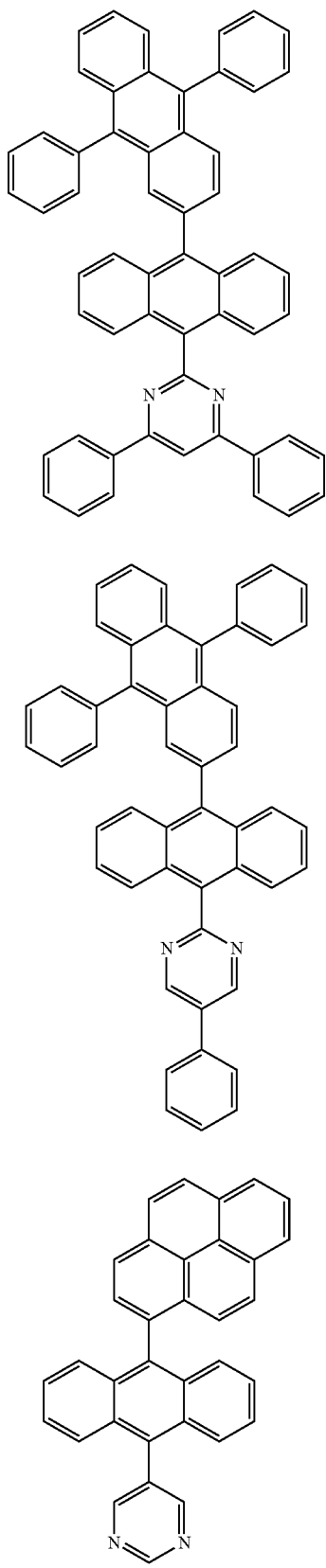
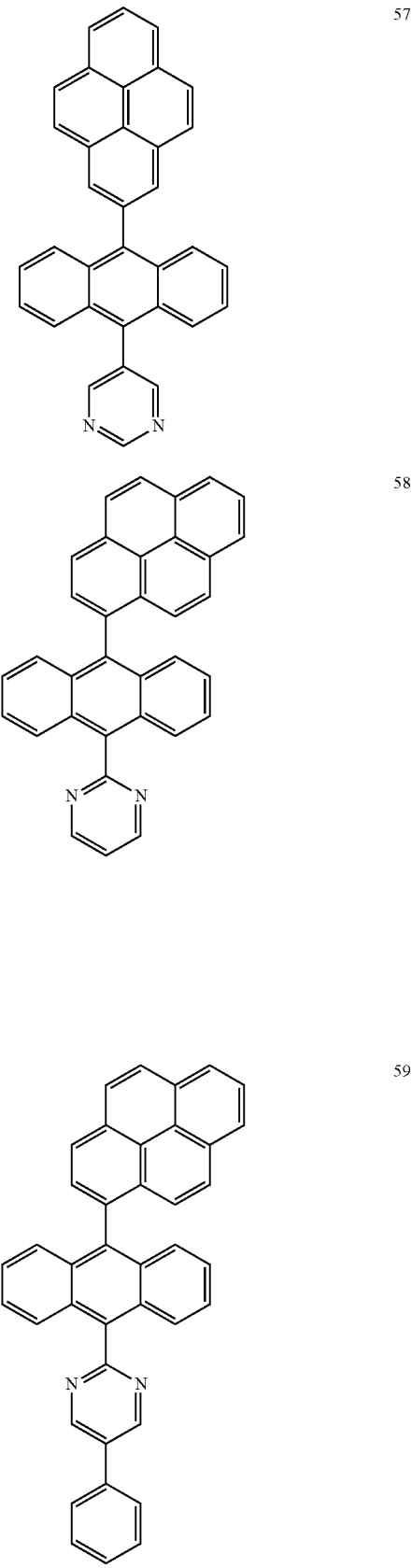

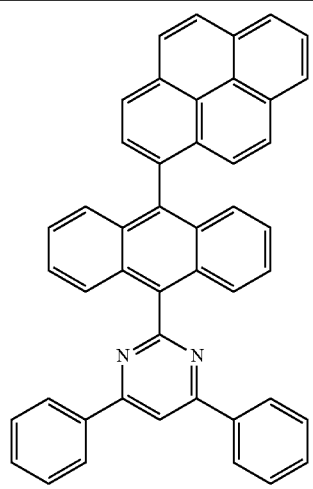
60
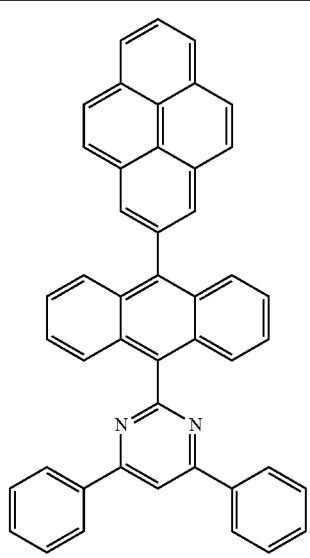
63
61
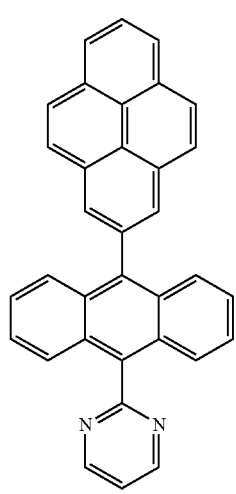 [SMILES: c1cnc(-c2c3ccccc3c(-c3cc4ccc5cccc6ccc(c3)c4c56)c3ccccc23)nc1]
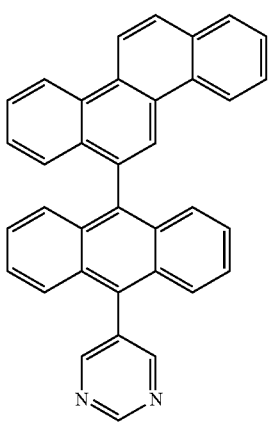 [SMILES: c1ccc2c(c1)ccc1c3ccccc3c(-c3c4ccccc4c(-c4cncnc4)c4ccccc34)cc21]
64
62
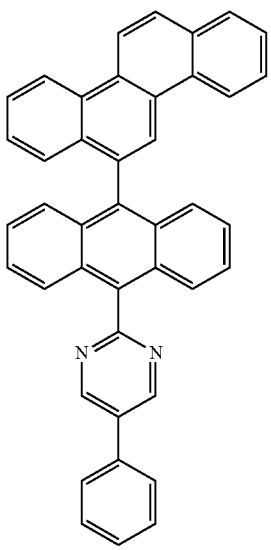 [SMILES: c1ccc(-c2cnc(-c3c4ccccc4c(-c4cc5c6ccccc6ccc5c5ccccc45)c4ccccc34)nc2)cc1]
65

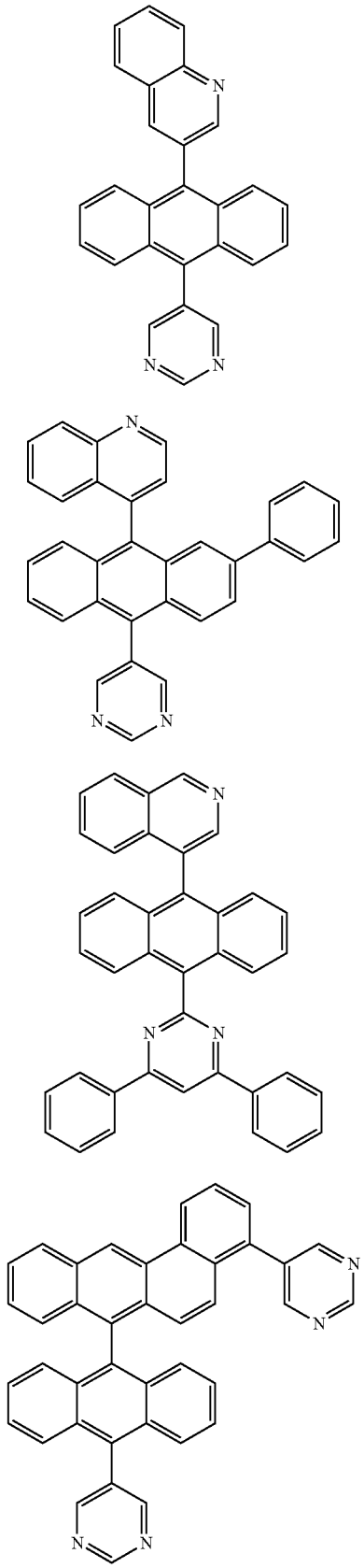

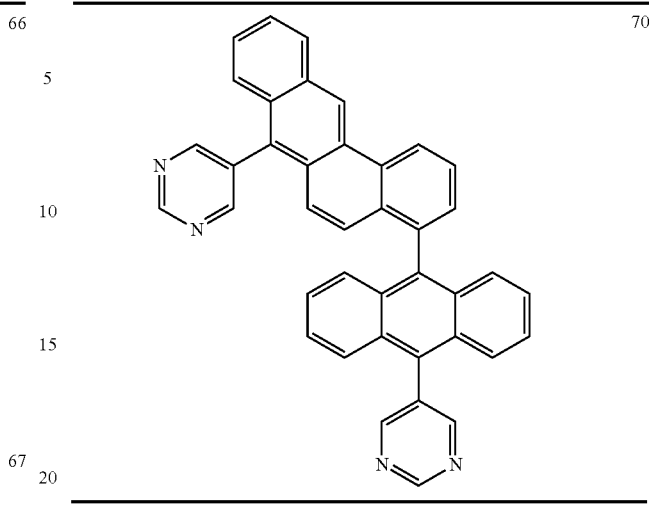

The synthesis of the compounds of the formula (1) according to the invention can be carried out by synthetic steps which are generally known to the person skilled in the art and is depicted in general terms in Schemes 1 and 2 below. A starting compound which can be used is the corresponding 9-bromoanthracene. Schemes 1 and 2 show syntheses of compounds which contain a pyrimidine group of the formula (2).

Scheme 1:

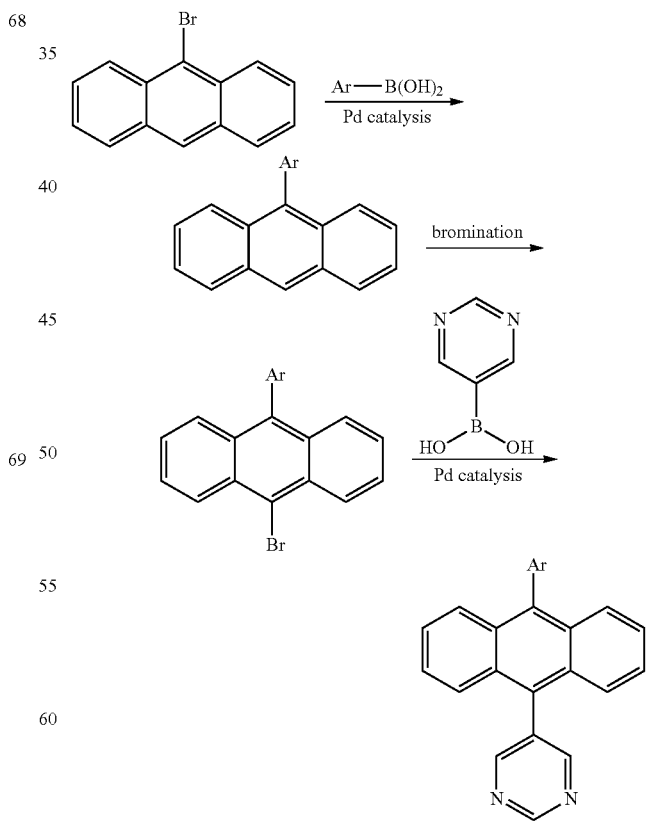

The Suzuki coupling in the first and third steps takes place under standard conditions, as are known to the person skilled in the art of organic chemistry, for example using Pd(PPh$_3$)$_4$ in toluene/water with addition of a base at elevated temperature. The bromination in the second step can be carried out, for example, using elemental bromine or using NBS. Alternatively, the compounds of the formula (1) according to the invention can also be synthesised in accordance with Scheme 2:

Scheme 2:

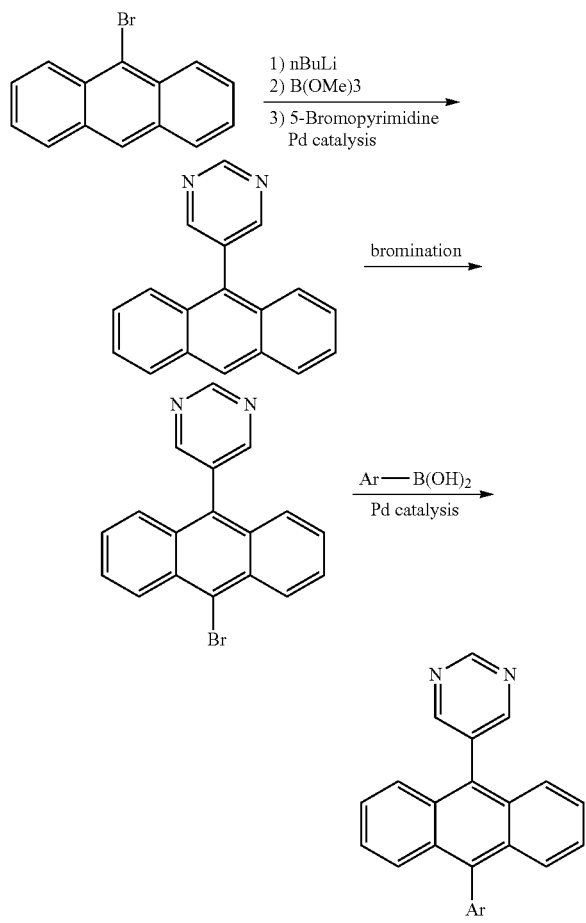

Instead of lithiation, the reaction with another reactive metal, for example magnesium, can also be carried out in a first step.

These reactions can also be carried out entirely analogously using a 2-bromo- or 2-boronopyrimidine derivative in order to synthesise compounds of the formula (1) which contain a pyrimidine group of the formula (3).

The compounds in Schemes 1 and 2 may also be substituted by one or more radicals, where these radicals are defined as described under formula (1). Ar in Schemes 1 and 2 stands for a condensed aryl or heteroaryl group, as defined for formula (1).

The present invention furthermore relates to a process for the preparation of a compound according to the invention, comprising the reaction of an anthracene derivative which is substituted by a reactive leaving group, in particular chlorine, bromine, iodine, triflate or tosylate, with a pyrimidine derivative which is substituted by a boronic acid group or a boronic acid ester group, or comprising the reaction of an anthracene derivative which is substituted by a boronic acid group or a boronic acid ester group with a pyrimidine derivative which is substituted by a reactive leaving group, in particular chlorine, bromine, iodine, triflate or tosylate.

The compounds according to the invention are suitable for use in an electronic device. An electronic device here is taken to mean a device which comprises at least one layer which comprises at least one organic compound. However, the component may also comprise inorganic materials or also layers which are built up completely from inorganic materials.

The present invention therefore furthermore relates to the use of the compounds according to the invention in an electronic device, in particular in an organic electroluminescent device.

An organic electroluminescent device is taken to mean a device which comprises an anode, a cathode and at least one emitting layer which is arranged between the anode and cathode, where at least one layer between the anode and cathode comprises at least one organic or organo-metallic compound. An organic electroluminescent device need not necessarily comprise only layers which are built up from organic or organometallic materials. Thus, it is also possible for one or more layers to comprise inorganic materials or to be built up entirely from inorganic materials. The compound according to the invention may be present here in one or more layers between the anode and cathode and/or it may be present in an additional layer on the anode or cathode as a so-called "optical out-coupling layer".

The present invention still furthermore relates to an electronic device comprising at least one compound according to the invention. The preferences indicated above likewise apply to the electronic devices.

The electronic device is preferably selected from the group consisting of organic electroluminescent devices (organic light-emitting diodes, OLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitized solar cells (ODSSCs), organic optical detectors, organic photoreceptors, organic field-quench devices (O-FQDs), light-emitting electrochemical cells (LECs), organic laser diodes (O-lasers) and "organic plasmon emitting devices" (D. M. Koller et al., Nature Photonics 2008, 1-4), but preferably organic electroluminescent devices (OLEDs).

The organic electroluminescent devices and the light-emitting electrochemical cells can be used for various applications, for example for monochromatic or polychromatic displays, for lighting applications or for medical applications, for example in phototherapy.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. Interlayers which have, for example, an exciton-blocking function and/or which control the charge balance in the device, may likewise be introduced between two emitting layers. Furthermore, the layers, in particular the charge-transport layers, may also be doped. The doping of the layers may be advantageous for improved charge transport. However, it should be pointed out that each of these layers does not necessarily have to be present and the choice of layers is always dependent on the compounds used.

The organic electroluminescent device here may comprise one emitting layer or a plurality of emitting layers. If a plurality of emission layers is present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 05/011013). It is possible here for all emitting layers to be fluorescent or for all emitting layers to be phosphorescent or for one or more emitting layers to be fluorescent and one or more other layers to be phosphorescent.

The compound according to the invention in accordance with the embodiments indicated above can be employed here in different layers, depending on the precise structure. Preference is given to an organic electroluminescent device comprising a compound of the formulae (1) or (4) to (6) or (4a) to (6a) in an electron-transport layer and/or in a hole-blocking layer and/or as matrix material for fluorescent emitters. The preferred embodiments indicated above also apply to the use of the materials in electronic devices.

The compound according to the invention is particularly preferably employed as electron-transport material in an electron-transport layer or in an electron-injection layer, in particular in an organic electroluminescent device.

The compound according to the invention can be used either as a pure layer or as a mixture with one or more further materials.

In a preferred embodiment of the invention, the compound according to the invention is used as a pure material in the electron-transport layer or in the electron-injection layer.

In a further preferred embodiment of the invention, the compound according to the invention is used in a mixture with a further electron-transport or electron-injection material in the electron-transport layer or in the electron-injection layer. This further material is preferably an organic alkali-metal compound.

The compound according to the invention is likewise preferably used as a pure material in the electron-transport layer, where a further layer which comprises an organic or inorganic alkali-metal compound is introduced between the electron-transport layer comprising the compound according to the invention and the cathode.

An organic alkali-metal compound in the sense of this invention is intended to be taken to mean a compound which contains at least one alkali metal, i.e. lithium, sodium, potassium, rubidium or caesium, and which furthermore contains at least one organic ligand or an organic counterion.

An inorganic alkali-metal compound is intended to be taken to mean a compound which contains at least one alkali metal, i.e. lithium, sodium, potassium, rubidium or caesium, and which furthermore contains only inorganic counterions, such as, for example, a halide or oxide.

Suitable organic alkali-metal compounds are, for example, the compounds disclosed in WO 2007/050301, WO 2007/050334 and EP 1144543. These are incorporated into the present application by way of reference.

Preferred organic alkali-metal compounds are the compounds of the following formula (28):

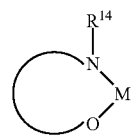

formula (28)

where $R^{14}$ has the same meaning as described above for $R^1$ to $R^{12}$, the curved line represents two or three atoms and bonds which are necessary to make up a 5- or 6-membered ring with M, where these atoms may also be substituted by one or more radicals $R^{12}$, and M represents an alkali metal selected from lithium, sodium, potassium, rubidium and caesium.

It is possible here for the complex of the formula (28) to be in monomeric form, as depicted above, or for it to be in the form of aggregates, for example comprising two alkali-metal ions and two ligands, four alkali-metal ions and four ligands, six alkali-metal ions and six ligands or other aggregates.

Preferred compounds of the formula (28) are the compounds of the following formulae (29) and (30):

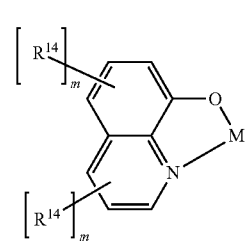

formula (29)

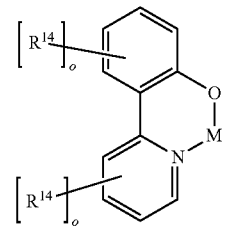

formula (30)

where the symbols and indices used have the meanings indicated above.

Further preferred organic alkali-metal compounds are the compounds of the following formula (31):

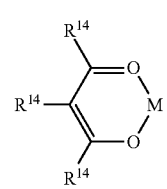

formula (31)

where the symbols used have the same meaning as described above.

The alkali metal is preferably selected from lithium, sodium and potassium, particularly preferably lithium and sodium, very particularly preferably lithium.

Particular preference is given to a compound of the formula (29), in particular where M=lithium. The indices m are furthermore very particularly preferably 0. The compound is thus very particularly preferably unsubstituted lithium quinolinate.
Examples of suitable organic alkali-metal compounds are the structures shown in the following table.
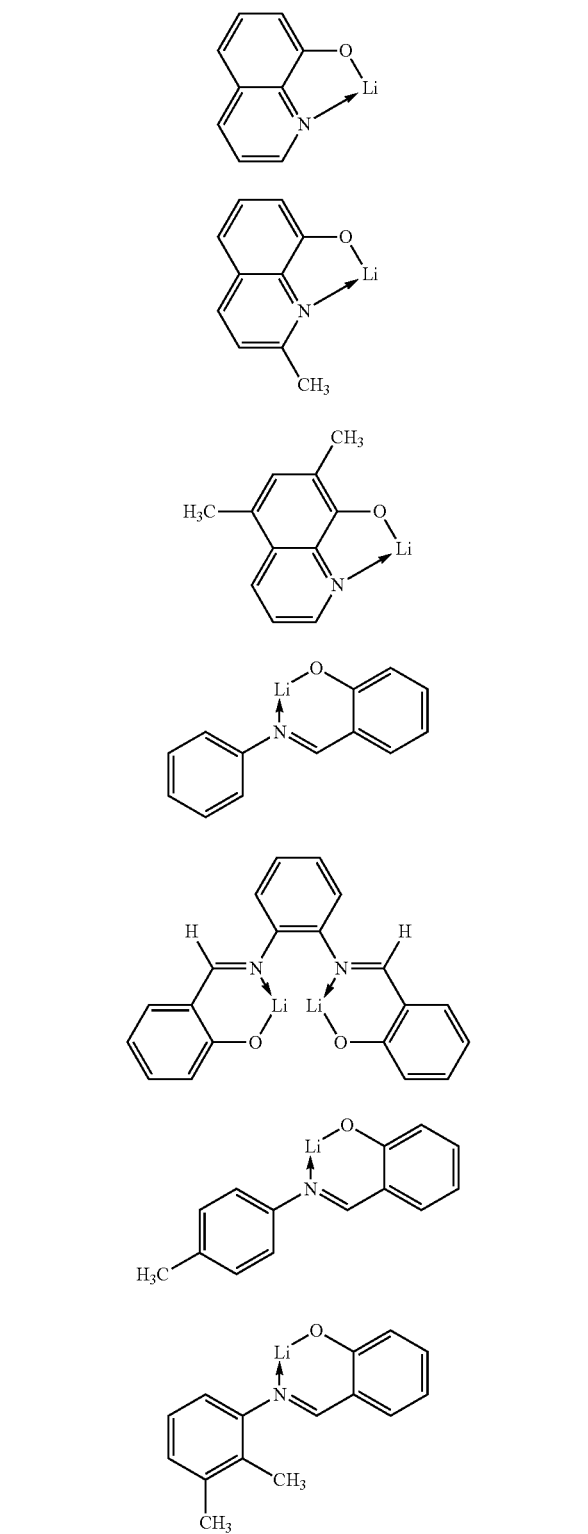
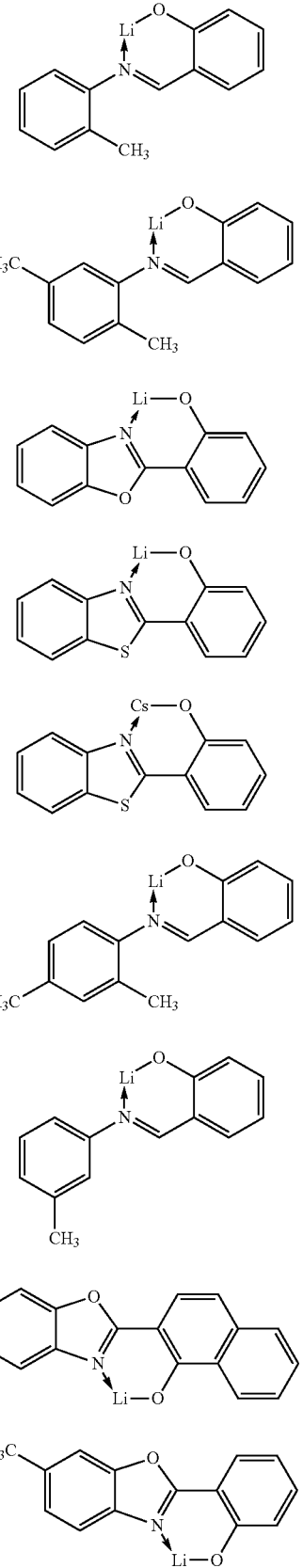

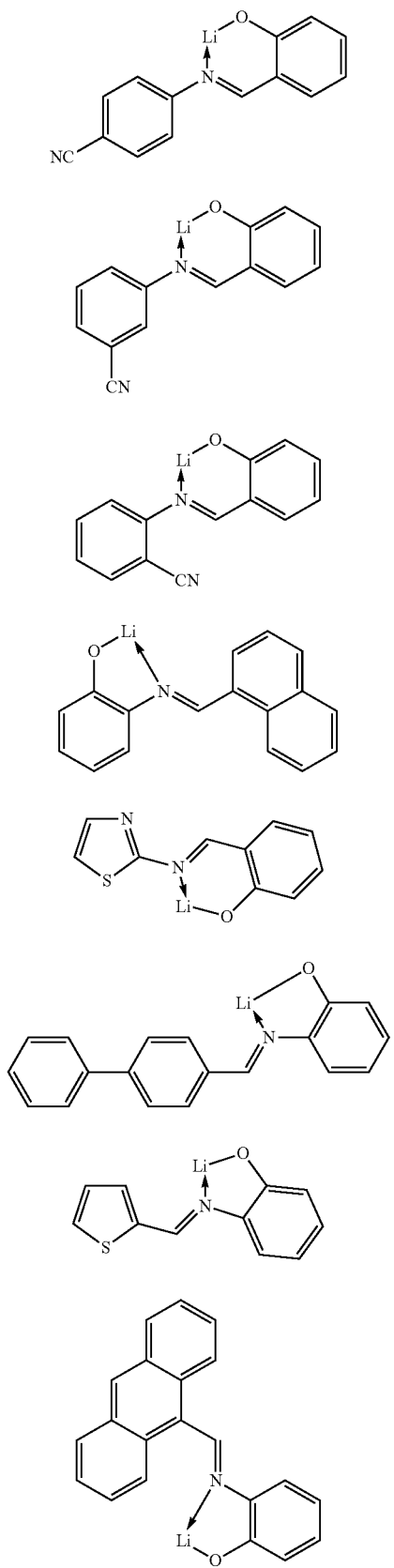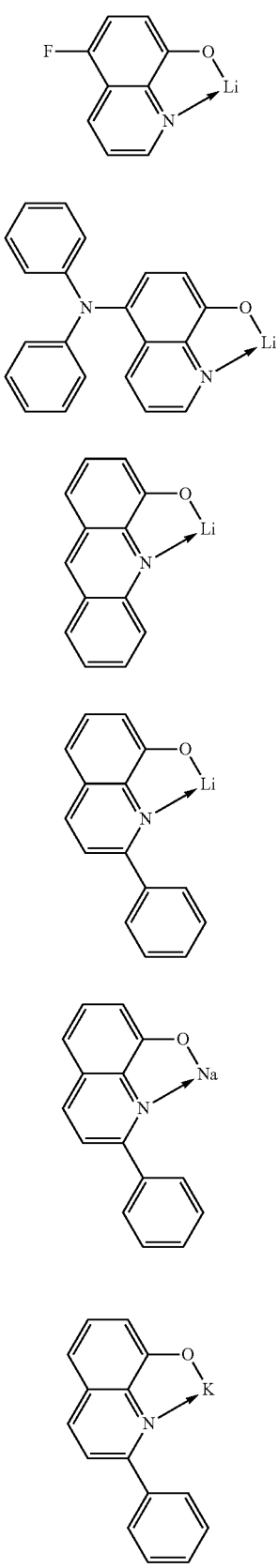

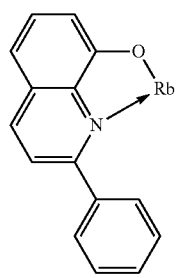
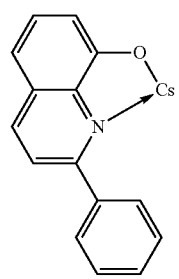
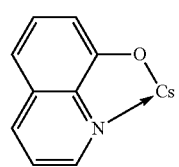
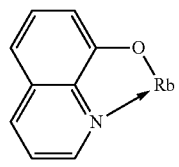
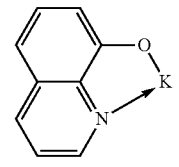
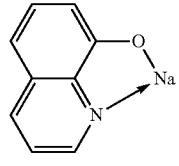
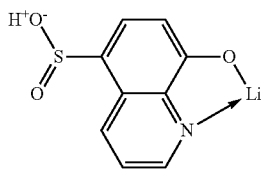
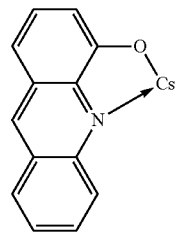
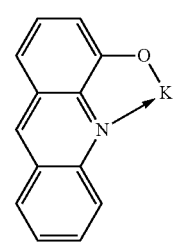
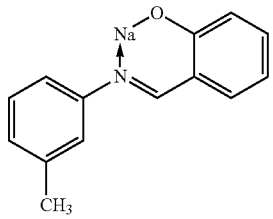
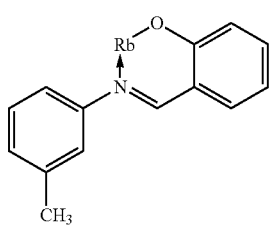
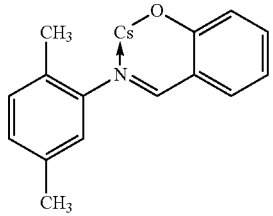
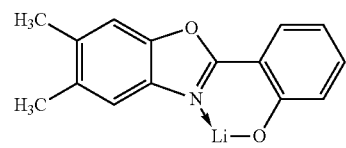
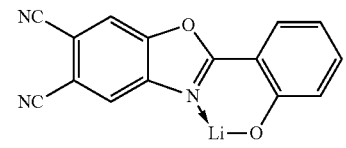
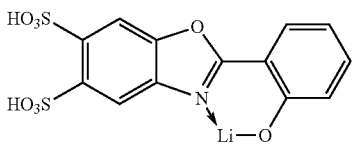

If the compound according to the invention and the organic alkali-metal compound are in the form of a mixture, the ratio of the compound according to the invention to the organic alkali-metal compound is preferably 20:80 to 80:20, particularly preferably 30:70 to 70:30, very particularly preferably 30:70 to 50:50, in particular 30:70 to 45:55.

If the compound according to the invention and the organic alkali-metal compound are in the form of a mixture, the layer thickness of this electron-transport layer is preferably between 3 and 150 nm, particularly preferably between 5 and 100 nm, very particularly preferably between 10 and 60 nm, in particular between 15 and 40 nm.

If the compound according to the invention and the organic alkali-metal compound are present in two successive layers, the layer thickness of the layer which comprises the compound according to the invention is preferably between 3 and 150 nm, particularly preferably between 5 and 100 nm, very particularly preferably between 10 and 60 nm, in particular between 15 and 40 nm. The layer thickness of the layer which comprises the organic alkali-metal compound and which is arranged between the layer comprising the compound according to the invention and the cathode is preferably between 0.5 and 20 nm, particularly preferably between 1 and 10 nm, very particularly preferably between 1 and 5 nm, in particular between 1.5 and 3 nm.

The emitting layer here can be a fluorescent or phosphorescent layer. In general, all known emitting materials and layers are suitable in combination with the electron-transport layer according to the invention, and the person skilled in the art will be able to combine any desired emitting layers with the electron-transport layer according to the invention without inventive step.

The cathode of the electroluminescent device according to the invention preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). In the case of multilayered structures, further metals which have a relatively high work function, such as, for example, Ag, can also be used in addition to the said metals, in which case combinations of the metals, such as, for example, Mg/Ag, Ca/Ag or Ba/Ag, are generally used. Preference is likewise given to metal alloys, in particular alloys comprising an alkali metal or alkaline-earth metal and silver, particularly preferably an alloy comprising Mg and Ag. It may also be preferred to introduce a thin interlayer of a material having a high dielectric constant between a metallic cathode and the organic semiconductor. This layer serves as electron-injection layer. Suitable for this purpose are, for example, alkali-metal or alkaline-earth metal fluorides, but also the corresponding oxides, carbonates or other salts, and also other metals (for example LiF, $Li_2O$, $LiBO_2$, $K_2SiO_3$, CsF, $Cs_2CO_3$, $BaF_2$, MgO, NaF, $Al_2O_3$, etc.), and also organic alkali-metal compounds, such as, for example, lithium quinolinate. The layer thickness of this layer is preferably between 0.5 and 5 nm.

The anode of the electroluminescent device according to the invention preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. At least one of the electrodes here must be transparent or partially transparent in order to facilitate the coupling-out of light. Preferred transparent or partially transparent anode materials are conductive mixed metal oxides. Particular preference is given to indium tin oxide (ITO) or indium zinc oxide (IZO). Preference is furthermore given to conductive, doped, organic materials, in particular conductive, doped polymers.

The device is correspondingly (depending on the application) structured, provided with contacts and finally hermetically sealed, since the lifetime of such devices is drastically shortened in the presence of water and/or air.

In general, all further materials as are employed in accordance with the prior art in organic electroluminescent devices can also be employed in combination with the electron-transport layer according to the invention.

Preference is furthermore given to an organic electroluminescent device, characterised in that one or more layers are applied by means of a sublimation process, in which the materials are applied by vapour deposition in vacuum sublimation units at an initial pressure of usually less than $10^{-5}$ mbar, preferably less than $10^{-6}$ mbar. However, it should be noted that the pressure may also be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), inkjet printing or nozzle printing. Soluble compounds are necessary for this purpose. High solubility can be achieved through suitable substitution of the compounds. Not only solutions of individual materials, but also solutions which comprise a plurality of compounds, for example matrix materials and dopants, can be applied here.

The organic electroluminescent device can also be produced as a hybrid system by applying one or more layers from solution and applying one or more other layers by vapour deposition. Thus, for example, it is possible to apply an emitting layer from solution and to apply an electron-transport layer comprising a compound according to the invention thereto, optionally in combination with an organic alkali-metal compound, by vacuum vapour deposition.

These processes are generally known to the person skilled in the art and can be applied by him without problems to organic electroluminescent devices comprising the compounds according to the invention.

For application from the liquid phase, formulations of the compounds according to the invention are necessary. The present invention therefore furthermore relates to a formulation, preferably a solution, dispersion or mini-emulsion, comprising at least one compound according to the invention and at least one solvent, preferably an organic solvent.

The present invention furthermore relates to mixtures comprising at least one compound according to the invention and at least one organic alkali-metal compound. The organic alkali-metal compound here is preferably selected from the compounds of the formulae (28) to (31) shown above.

The organic electroluminescent devices according to the invention have the following surprising advantages over the prior art:
1. The organic electroluminescent devices according to the invention have very high efficiency. The improved efficiency is possibly attributable to improved electron injection from the electron-transport layer into the emitting layer.
2. The organic electroluminescent devices according to the invention at the same time have a comparable or improved lifetime.
3. The organic electroluminescent devices according to the invention at the same time have a reduced operating voltage. The reduced operating voltage may be attributable to improved electron injection from the electron-transport layer into the emitting layer.

The invention is described in greater detail by the following examples without wishing it to be restricted thereby. The person skilled in the art will be able, without being inventive, to prepare further compounds according to the invention and use them in organic electronic devices.

EXAMPLES

Example 1: Synthesis of 5-(10-benzo[a]anthracen-4-ylanthracen-9-yl)-pyrimidine a) 4-Anthracen-9-ylbenzo[a]anthracene

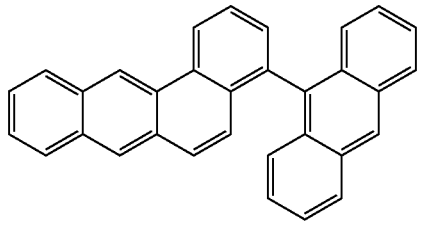 [SMILES: c1ccc2cc3c(ccc4c(-c5c6ccccc6cc6ccccc56)cccc43)cc2c1]

49.7 g (184 mmol) of 9-bromoanthracene, 50 g (184 mmol) of 2-benzo[a]-anthraceneboronic acid and 88.9 g (386 mmol) of $K_3PO_4$ are suspended in 900 ml of toluene, 180 ml of 1,4-dioxane and 1100 ml of water. 0.42 g (2 mmol) of Pd(OAc)$_2$ and 11 ml of a 1 M tri-tert-butylphosphine solution are added to this suspension. The reaction mixture is heated under reflux for 16 h. After cooling, the reaction mixture is filtered through silica gel, and the organic phase is separated off, washed three times with 200 ml of water and subsequently evaporated to dryness. The residue is recrystallised from toluene. Yield 48 g, 65% of theory.

b) 4-(10-Bromoanthracen-9-yl)benzo[a]anthracene

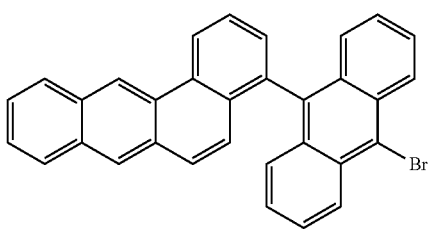 [SMILES: Brc1c2ccccc2c(-c2cccc3c2ccc2cc4ccccc4cc23)c2ccccc12]

30.9 g (76.4 mmol) of 4-anthracen-9-ylbenzo[a]anthracene are initially introduced in 500 ml of chloroform, and 1.2 g (7.6 mmol) of iron(III) chloride are added. A solution of 15.6 g (87.86 mmol) of NBS in 20 ml of chloroform is subsequently added dropwise at 0° C. with exclusion of light, and the mixture is stirred at this temperature for a further 2 h. 150 ml of water are subsequently added to the mixture, which is then extracted with ethyl acetate. The organic phase is dried over MgSO$_4$, and the solvents are removed in vacuo. The product is recrystallised from toluene. Yield: 20.4 g, 55% of theory, purity according to HPLC about 98%.

c) 5-(10-Benzo[a]anthracen-4-ylanthracen-9-yl)pyrimidine

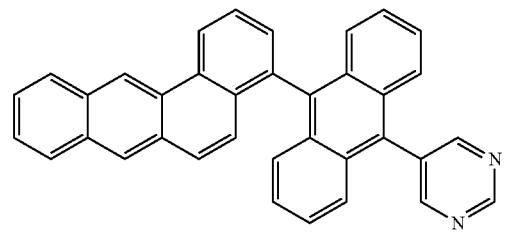 [SMILES: c1ccc2cc3c(ccc4c(-c5c6ccccc6c(-c6cncnc6)c6ccccc56)cccc43)cc2c1]

5-Pyrimidineboronic acid is prepared analogously to *Org. Biomol. Chem.*, 2004, 2, 852. 20 g (41.4 mmol) of 10-(bromoanthracen-9-yl)benzo[a]-anthracene and 7.2 g (57.9 mmol) of 5-pyrimidineboronic acid are suspended in 600 ml of ethylene glycol dimethyl ether and 150 ml of EtOH. 200 ml of a 0.5 M Na$_2$CO$_3$ solution are added to the reaction mixture. 500 mg (0.414 mmol) of Pd(PPh$_3$)$_4$ are added to this suspension, and the mixture is heated under reflux for 12 h. After cooling, the precipitated solid is filtered off with suction, washed with water and ethanol and dried. The residue is extracted with hot toluene, recrystallised from toluene and finally sublimed in a high vacuum. The purity is 99.9%. Yield: 10 g, 50% of theory.

Example 2: Synthesis of 2-(10-benzo[a]anthracen-4-ylanthracen-9-yl)-5-phenylpyrimidine a) 2-Anthracen-9-yl-5-phenylpyrimidine

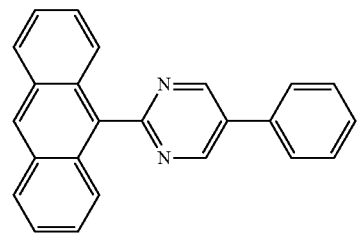 [SMILES: c1ccc(-c2cnc(-c3c4ccccc4cc4ccccc34)nc2)cc1]

36.1 g (140.4 mmol) of 9-bromoanthracene are dissolved in 600 ml of dry THF and cooled to −78° C. At this temperature, 66.4 ml (165.9 mmol/2.5 M in hexane) of n-butyllithium are added over the course of about 20 min., and the mixture is subsequently stirred at −78° C. for a further 2.5 h. 45.1 ml (191.4 mmol) of trimethyl borate are added as rapidly as possible at this temperature, and the reaction is slowly allowed to come to room temperature (about 18 h).

30 g (127.6 mmol) of 2-bromo-5-phenylpyrimidine are dissolved in a degassed mixture of 800 ml of toluene and 68 ml of tetraethylammonium hydroxide, and 4.4 g (3.83 mmol) of Pd(PPh$_3$)$_4$ are added. The 9-boronoanthracene solution is added dropwise thereto. The reaction mixture is heated under reflux for 8 h. After cooling, dichloromethane is added, the water phase is separated off, and the organic phase is concentrated by azeotropic distillation with toluene. The reaction product is recrystallised from toluene, giving 35 g (82%) of 2-anthracen-9-yl-5-phenylpyrimidine.

b) 2-(10-Bromoanthracen-9-yl)-5-phenylpyrimidine

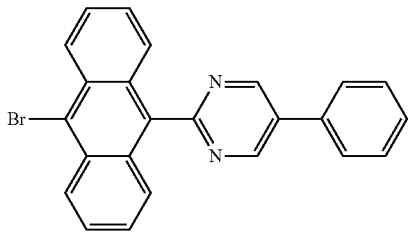 [SMILES: Brc1c2ccccc2c(-c2ncc(-c3ccccc3)cn2)c2ccccc12]

35 g (105.3 mmol) of 2-anthracen-9-yl-5-phenylpyrimidine are initially introduced in 500 ml of chloroform. A solution of 20.7 g (115.8 mmol) of NBS in 500 ml of chloroform is subsequently added dropwise at 0° C. with exclusion of light, and the mixture is stirred at this temperature for a further 4 h. 150 ml of water are subsequently added to the mixture, which is then extracted with ethyl acetate. The organic phase is dried over MgSO$_4$, and the solvents are removed in vacuo. The product is recrystallised from toluene. Yield: 32.5 g, 75% of theory, purity according to HPLC about 98%.

c) 2-(10-Benzo[a]anthracen-4-ylanthracen-9-yl)-5-phenylpyrimidine

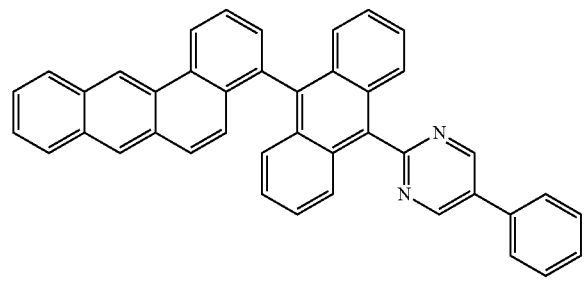 [SMILES: c1ccc(-c2cnc(-c3c4ccccc4c(-c4cccc5c4ccc4cc6ccccc6cc45)c4ccccc34)nc2)cc1]

30 g (72.94 mmol) of 2-(10-bromoanthracen-9-yl)-5-phenylpyrimidine, 21.8 g (80.24 mmol) of 2-benzo[a]anthraceneboronic acid and 32 g (153 mmol) of K$_3$PO$_4$ are suspended in 600 ml of toluene, 150 ml of 1,4-dioxane and 150 ml of water. 2.1 g (1.82 mmol) of Pd(PPh$_3$)$_4$ are added to this suspension. The reaction mixture is heated under reflux for 16 h. After cooling, dichloromethane is added to the reaction mixture, the water phase is separated off, and the organic phase is concentrated by azeotropic distillation with toluene and subsequently evaporated to dryness. The residue is recrystallised from toluene and finally sublimed in a high vacuum. The purity is 99.9%. Yield: 20 g, 50% of theory.

Example 3: Synthesis of 5-(10-phenanthren-3-ylanthracen-9-yl)-2-pyridin-2-ylpyrimidine a) 5-Bromo-2-pyridin-2-ylpyrimidine

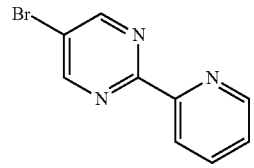 [SMILES: Brc1cnc(-c2ccccn2)nc1]

14.6 ml (150 mmol) of 2-bromopyridine are dissolved in 700 ml of dry THF and cooled to −78° C. At this temperature, 66.0 ml (165 mmol/2.5 M in hexane) of n-BuLi are added over the course of about 20 min., and the mixture is subsequently stirred at −78° C. for a further 2.5 h. 44.8 ml (165 mmol) of tributyltin chloride are added as rapidly as possible at this temperature, and the reaction is slowly allowed to come to room temperature (about 18 h). 150 ml of NH$_4$Cl solution are subsequently added to the reaction mixture, which is then extracted with ethyl acetate. The organic phase is dried over MgSO$_4$, and the solvents are removed in vacuo. Yield: 44 g of 2-(tributyltin)pyridine, 80% of theory.

30 g (108.6 mmol) of 2-(tributyltin)pyridine are suspended in 600 ml of xylene, and 31 g (108.6 mmol) of 2-iodo-5-bromopyrimidine are added. 3.8 g (5.43 mmol) of Pd(PPh$_3$)$_2$Cl$_2$ and 2.85 g (10.86 mmol) of triphenyl-phosphine are added to this suspension. The reaction mixture is heated under reflux for 16 h. After cooling, dichloromethane is added to the reaction mixture, the water phase is separated off, and the organic phase is concentrated by azeotropic distillation with toluene and subsequently evaporated to dryness. The residue is recrystallised from toluene. Yield: 20 g, 78% of theory.

b) 5-Anthracen-9-yl-2-pyridin-2-ylpyrimidine

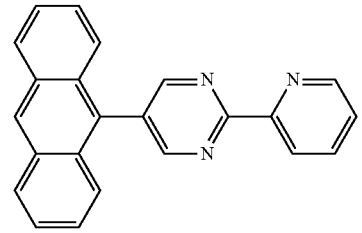 [SMILES: c1ccc(-c2ncc(-c3c4ccccc4cc4ccccc34)cn2)nc1]

20.6 g (80 mmol) of 9-bromoanthracene are dissolved in 400 ml of dry THF and cooled to −78° C. At this temperature, 36.8 ml (92 mmol/2.5 M in hexane) of n-BuLi are added over the course of about 20 min., and the mixture is subsequently stirred at −78° C. for a further 2.5 h. 26.4 ml (112 mmol) of triisopropyl borate are added as rapidly as possible t this temperature, and the reaction is slowly allowed to come to room temperature (about 18 h).

18.9 g (80 mmol) of 5-bromo-2-pyridin-2-ylpyrimidine are dissolved in a degassed mixture of 400 ml of toluene and 42 ml of tetraethylammonium hydroxide (20%), and 2.77 g (2.4 mmol) of Pd(PPh$_3$)$_4$ are added. The 9-boronoanthracene solution is added dropwise thereto. The reaction mixture is heated under reflux for 8 h. After cooling, dichloromethane is added, the water phase is separated off, and the organic phase is concentrated by azeotropic distillation with toluene. The reaction product is recrystallised from toluene, giving 23 g (85%) of 5-anthracen-9-yl-2-pyridin-2-ylpyrimidine.

c) 5-(10-Bromoanthracen-9-yl)-2-pyridin-2-ylpyrimidine

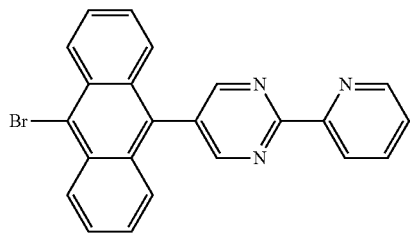 [SMILES: Brc1c2ccccc2c(-c2cnc(-c3ccccn3)nc2)c2ccccc12]

20 g (68 mmol) of 5-anthracen-9-yl-2-pyridin-2-ylpyrimidine are initially introduced in 300 ml of chloroform. A solution of 13.31 g (74.8 mmol) of NBS in 200 ml of chloroform is subsequently added dropwise at 0° C. with exclusion of light, and the mixture is stirred at this temperature for a further 4 h. 150 ml of water are subsequently added to the mixture, which is then extracted with ethyl acetate. The organic phase is dried over MgSO₄, and the solvents are removed in vacuo. The product is recrystallised from toluene. Yield: 22.4 g, 80% of theory, purity according to HPLC about 98%.

d) 5-(10-Phenanthren-3-ylanthracen-9-yl)-2-pyridin-2-ylpyrimidine

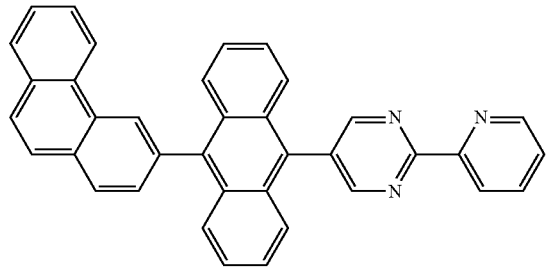 [SMILES: c1ccc(-c2ncc(-c3c4ccccc4c(-c4ccc5ccc6ccccc6c5c4)c4ccccc34)cn2)nc1]

20 g (77.8 mmol) of 3-bromophenanthrene are dissolved in 400 ml of dry THF and cooled to −78° C. At this temperature, 40.5 ml (101.1 mmol/2.5 M in hexane) of n-BuLi are added over the course of about 20 min., and the mixture is subsequently stirred at −78° C. for a further 2.5 h. 28.7 ml (124.4 mmol) of triisopropyl borate are added as rapidly as possible at this temperature, and the reaction is slowly allowed to come to room temperature (about 18 h). 100 ml of NH₄Cl solution are subsequently added to the reaction mixture, which is then extracted with ethyl acetate. The organic phase is dried over MgSO₄, and the solvents are removed in vacuo. Yield: 14 g of 3-phenanthreneboronic acid, 80% of theory.

22 g (53.36 mmol) of 5-(10-bromoanthracen-9-yl)-2-pyridin-2-ylpyrimidine, 13 g (58.7 mmol) of 3-phenanthreneboronic acid and 23.8 g (112 mmol) of K₃PO₄ are suspended in 200 ml of toluene, 200 ml of 1,4-dioxane and 120 ml of water. 1.85 g (1.6 mmol) of Pd(PPh₃)₄ are added to this suspension. The reaction mixture is heated under reflux for 16 h. After cooling, dichloromethane is added to the reaction mixture, the water phase is separated off, and the organic phase is concentrated by azeotropic distillation with toluene and subsequently evaporated to dryness. The residue is recrystallised from toluene and finally sublimed in a high vacuum. The purity is 99.9%. Yield: 16 g, 60% of theory.

Example 4: Production of OLEDs

OLEDs according to the invention and OLEDs in accordance with the prior art are produced by a general process in accordance with WO 2004/058911, which is adapted to the circumstances described here (layer-thickness variation, materials used).

The results for various OLEDs are presented in OLED Examples 1-23 below (see Tables 1 and 2). Glass plates coated with structured ITO (indium tin oxide) in a thickness of 50 nm form the substrates to which the OLEDs are applied. The OLEDs basically have the following layer structure: substrate ITO/hole-transport layer (HTL, 140 nm)/interlayer (IL, 5 nm)/electron-blocking layer (EBL, 20 nm)/emission layer (EML (H1+x % of D1), z nm)/electron-transport layer (ETL, y nm)/optional electron-injection layer (EIL, x nm) and finally a cathode. The cathode is formed by an aluminium layer with a thickness of 100 nm. The precise structure of the OLEDs is shown in Table 1. The materials used for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or materials in a certain proportion by volume by coevaporation. An expression such as H1:D1 (95%:5%) here means that material H1 is present in the layer in a proportion by volume of 95% and D1 is present in the layer in a proportion by volume of 5%. Analogously, the electron-transport layer may also consist of a mixture of two materials.

The OLEDs are characterised by standard methods. For this purpose, the electroluminescence spectra, current-voltage-luminance characteristic lines (IUL characteristic lines) and the lifetime are measured. The lifetime is defined as the time after which the luminous density has dropped to a certain proportion from a certain initial luminous density $I_0$. The expression LD50 means that the said lifetime is the time by which the luminous density has dropped to $0.5 \cdot I_0$ (to 50%), from 6000 cd/m² to 3000 cd/m² in the examples for blue (y<0.25) and from 4000 cd/m² to 2000 cd/m² in the other examples. The current efficiency (cd/A) and the power efficiency (lm/W) are calculated from the IUL characteristic lines.

The compounds according to the invention can be employed, inter alia, as electron-transport material in an electron-transport layer (ETL) for fluorescent and phosphorescent OLEDs. Compounds ETL2, ETL3 and ETL4 according to the invention are used here. Compounds ETL1 and ETL5 are used as comparison in accordance with the prior art. The results for the OLEDs are summarized in Table 2. Examples 1-5 and 21-23 show OLEDs comprising materials in accordance with the prior art and serve as comparative examples. The OLEDs according to Examples 6-20 according to the invention exhibit the advantages on use of compounds of the formula (1) according to the invention.

The use of compounds according to the invention enables, compared with the prior art, improvements to be achieved in the operating voltage, the efficiency and the lifetime of the components.

Compared with the reference components, the electrical characteristic data are better in all cases. With an otherwise identical layer structure, the components according to the invention exhibit improved performance data.

TABLE 1

Structure of the OLEDs

| Ex. | EML | ETL | EIL |
|---|---|---|---|
| 1 (comp.) | H1:D1 (95%:5%) 30 nm | ETL1 20 nm | EIL1 3 nm |
| 2 (comp.) | H1:D1 (95%:5%) 30 nm | ETL1:EIL1 (50%:50%) 20 nm | — |
| 3 (comp.) | H2:D2 (85%:15%) 40 nm | ETL1 30 nm | EIL2 1 nm |
| 4 (comp.) | H2:D2 (85%:15%) 40 nm | ETL1 30 nm | EIL1 3 nm |
| 5 (comp.) | H2:D2 (85%:15%) 40 nm | ETL1:EIL1 (50%:50%) 30 nm | — |
| 6 | H1:D1 (95%:5%) 30 nm | ETL2 20 nm | EIL1 3 nm |
| 7 | H1:D1 (95%:5%) 30 nm | ETL3 20 nm | EIL1 3 nm |
| 8 | H1:D1 (95%:5%) 30 nm | ETL4 20 nm | EIL1 3 nm |
| 9 | H1:D1 (95%:5%) 30 nm | ETL2:EIL1 (50%:50%) 20 nm | |
| 10 | H1:D1 (95%:5%) 30 nm | ETL3:EIL1 (50%:50%) 20 nm | |
| 11 | H1:D1 (95%:5%) 30 nm | ETL4:EIL1 (50%:50%) 20 nm | |
| 12 | H1:D1 (95%:5%) 30 nm | ETL2:EIL1 (30%:70%) 20 nm | |
| 13 | H2:D2 (85%:15%) 40 nm | ETL2 20 nm | EIL2 1 nm |
| 14 | H2:D2 (85%:15%) 40 nm | ETL3 20 nm | EIL2 1 nm |
| 15 | H2:D2 (85%:15%) 40 nm | ETL4 20 nm | EIL2 1 nm |
| 16 | H2:D2 (85%:15%) 40 nm | ETL2:EIL1 (50:50) 20 nm | |
| 17 | H2:D2 (85%:15%) 40 nm | ETL3:EIL1 (50%:50%) 20 nm | |
| 18 | H2:D2 (85%:15%) 40 nm | ETL4:EIL1 (50%:50%) 20 nm | |
| 19 | H2:D2 (85%:15%) 40 nm | ETL2 20 nm | EIL1 3 nm |
| 20 | H2:D2 (85%:15%) 40 nm | ETL4 20 nm | EIL1 3 nm |
| 21 (comp.) | H2:D2 (85%:15%) 40 nm | ETL5:EIL1 (50%:50%) 30 nm | |
| 22 (comp.) | H2:D2 (85%:15%) 40 nm | ETL5 30 nm | EIL2 1 nm |
| 23 (comp.) | H2:D2 (85%:15%) 40 nm | ETL5 30 nm | EIL1 3 nm |

TABLE 2

Results for the OLEDs

| Ex. | Voltage [V] for 1000 cd/m$^2$ | Efficiency [cd/A] at 1000 cd/m$^2$ | CIE x/y at 1000 cd/m$^2$ | | LD50 I = 6000 cd/m$^2$ |
|---|---|---|---|---|---|
| 1 (comp.) | 4.9 | 6.6 | 0.14 | 0.15 | 250 |
| 6 | 4.3 | 7.0 | 0.14 | 0.14 | 290 |
| 7 | 4.6 | 6.9 | 0.14 | 0.15 | 270 |
| 8 | 4.4 | 7.2 | 0.14 | 0.14 | 310 |
| 2 (comp.) | 5.1 | 6.9 | 0.14 | 0.15 | 300 |
| 9 | 4.4 | 8.4 | 0.14 | 0.14 | 330 |
| 10 | 4.8 | 8.3 | 0.14 | 0.15 | 320 |
| 11 | 4.6 | 8.1 | 0.14 | 0.14 | 370 |
| 12 | 4.6 | 7.9 | 0.14 | 0.14 | 350 |
| 3 (comp.) | 3.7 | 46.3 | 0.33 | 0.62 | 900 |
| 22 (comp.) | 3.9 | 43.4 | 0.33 | 0.61 | 800 |
| 13 | 3.4 | 49.1 | 0.33 | 0.62 | 1900 |
| 14 | 3.6 | 48.5 | 0.33 | 0.62 | 1700 |
| 15 | 3.5 | 48.7 | 0.33 | 0.62 | 2100 |
| 4 (comp.) | 4.1 | 43.3 | 0.33 | 0.62 | 1070 |
| 23 (comp.) | 4.3 | 41.2 | 0.33 | 0.61 | 950 |
| 19 | 3.9 | 45.1 | 0.33 | 0.62 | 1450 |
| 20 | 3.5 | 50.3 | 0.33 | 0.62 | 1600 |
| 5 (comp.) | 3.6 | 44.5 | 0.33 | 0.62 | 1100 |
| 21 (comp.) | 3.8 | 41.3 | 0.33 | 0.62 | 900 |
| 16 | 3.4 | 49.2 | 0.33 | 0.62 | 2100 |
| 17 | 3.5 | 47.2 | 0.33 | 0.62 | 1700 |
| 18 | 3.3 | 53.7 | 0.33 | 0.62 | 3100 |

TABLE 3

Structural formulae of the materials used

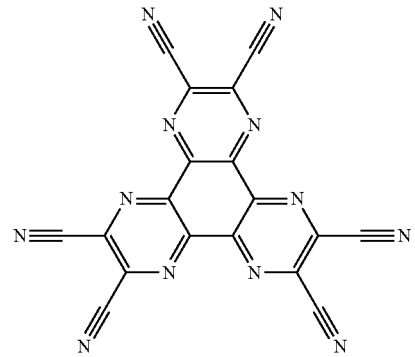 [SMILES: N#Cc1nc2c3nc(C#N)c(C#N)nc3c3nc(C#N)c(C#N)nc3c2nc1C#N]

IL

TABLE 3-continued
Structural formulae of the materials used
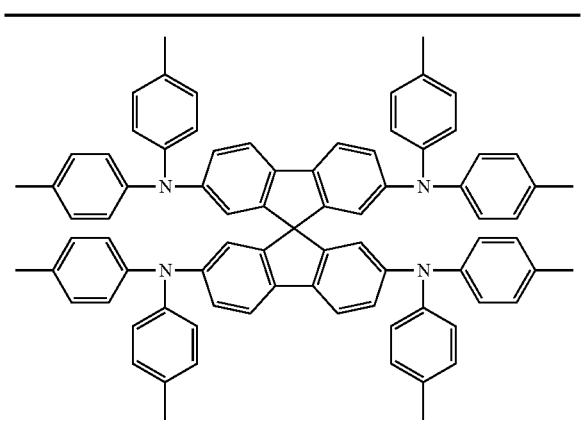
HTL
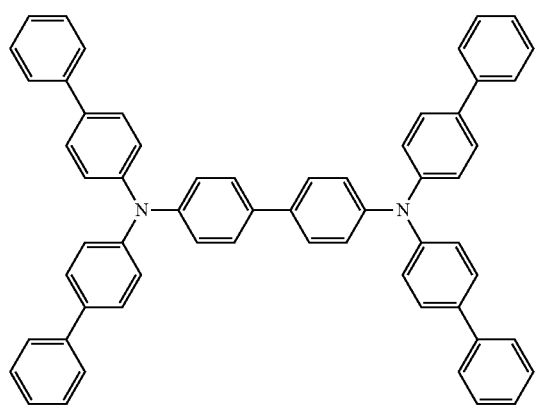 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
EBL
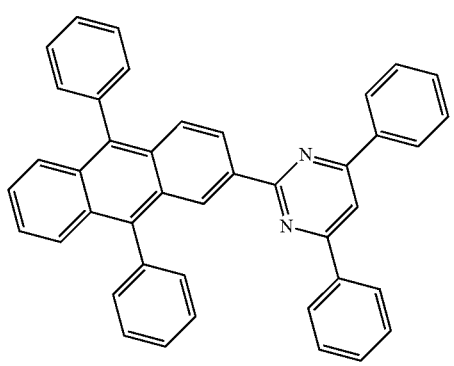 [SMILES: c1ccc(-c2cc(-c3ccccc3)nc(-c3ccc4c(-c5ccccc5)c5ccccc5c(-c5ccccc5)c4c3)n2)cc1]
ETL1 (comparison)
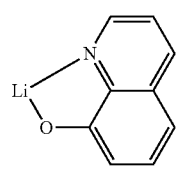
EIL1
TABLE 3-continued
Structural formulae of the materials used
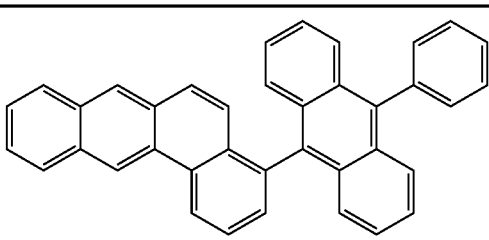
H1
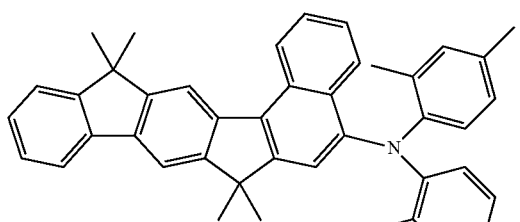
D1
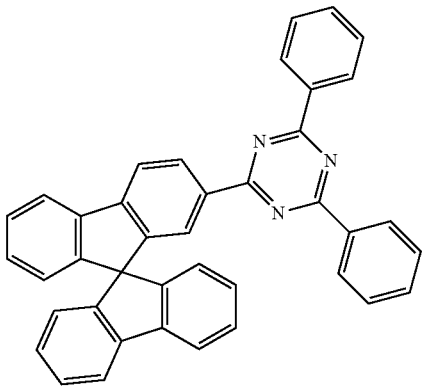 [SMILES: c1ccc(-c2nc(-c3ccccc3)nc(-c3ccc4c(c3)C3(c5ccccc5-c5ccccc53)c3ccccc3-4)n2)cc1]
H2
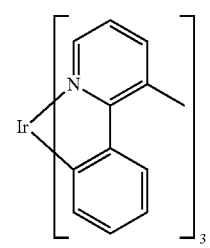
D2
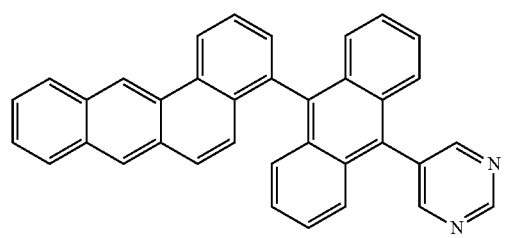 [SMILES: c1ccc2cc3c(ccc4c(-c5c6ccccc6c(-c6cncnc6)c6ccccc56)cccc43)cc2c1]
ETL2

TABLE 3-continued

Structural formulae of the materials used

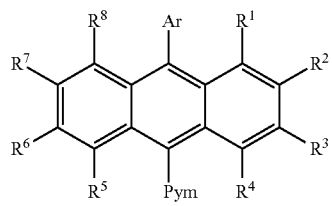

ETL3

ETL4

ETL5 (comparison)

LiF is used as EIL2.

The invention claimed is:

1. A compound of formula (1), formula (1)

wherein:

Pym is selected from the group consisting of formula (2) and formula (3),

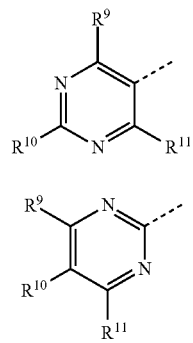

formula (2)

formula (3)

wherein the dashed bond indicates the bond to the anthracene;

Ar is selected from one group of formulae (9) to (25)

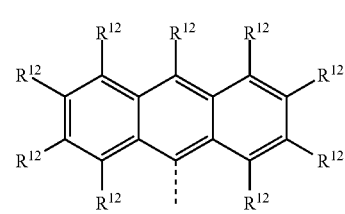

formula 9

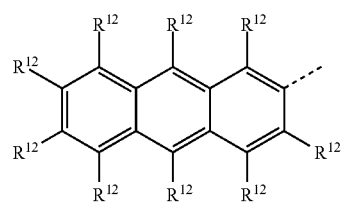

formula (10)

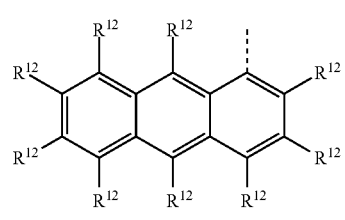

formula (11)

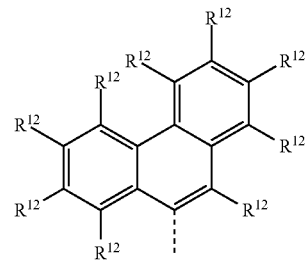

formula (12)

formula (13)
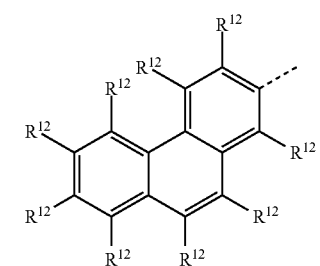
formula (14)
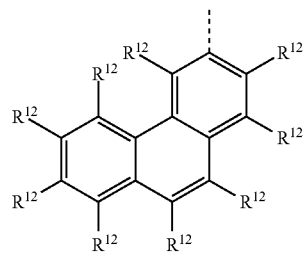
formula (15)
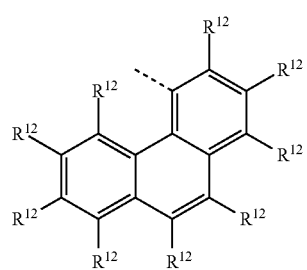
formula (16)
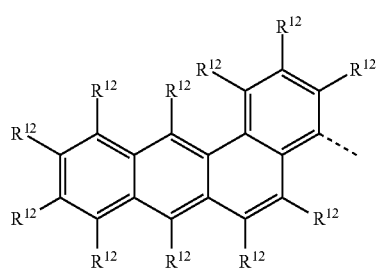
formula (17)
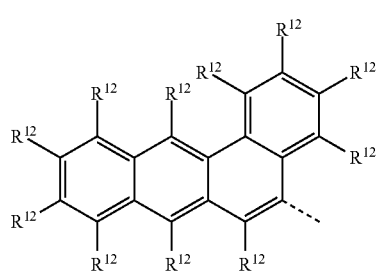
formula (18)
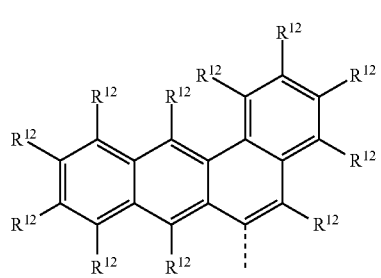
formula (19)
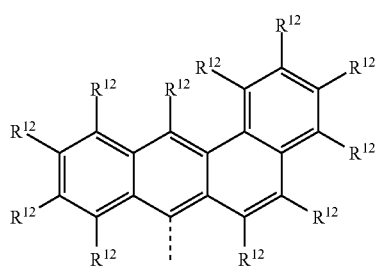
formula (20)
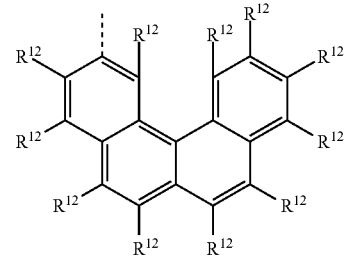
formula (21)
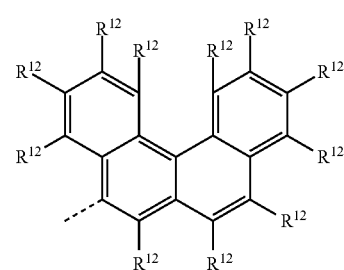
formula (22)
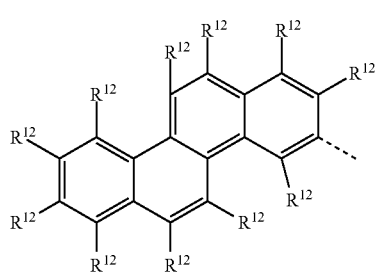
formula (23)
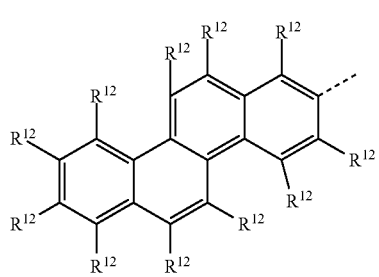
formula (24)
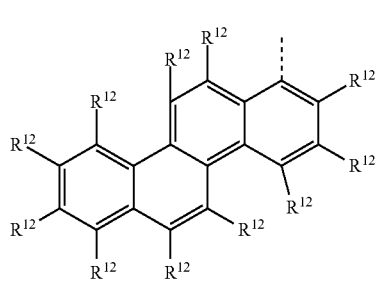

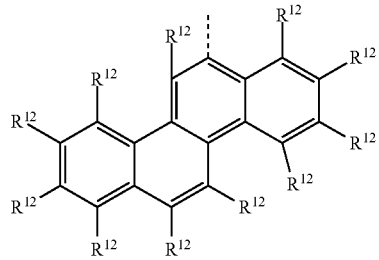

formula (25)

wherein the dashed bond is the position of the link to the anthracene of the compound of formula (1);

$R^1$, $R^2$, $R^3$, $R^4$, $R^5$, $R^6$, $R^7$, $R^8$, $R^9$, $R^{10}$, $R^{11}$, and $R^{12}$ are, identically or differently on each occurrence, H, D, F, Cl, Br, I, CHO, $N(R^{13})_2$, $N(Ar^1)_2$, $B(Ar^1)_2$, $Si(R^{13})_2$, $Si(Ar^1)_2$, $C(=O)Ar^1$, $P(=O)(Ar^1)_2$, $S(=O)Ar^1$, $S(=O)_2Ar^1$, $CR^{13}=CR^{13}Ar^1$, CN, $NO_2$, $Si(R^{13})_3$, $B(OR^{13})_2$, $B(R^3)_2$, $B(N(R^3)_2)_2$, $OSO_2R^{13}$, a straight-chain alkyl, alkenyl, alkynyl, alkoxy or thioalkoxy group having 1 to 40 C atoms, or a branched or cyclic alkyl, alkenyl, alkynyl, alkoxy or thioalkoxy group having 3 to 40 C atoms, each of which is optionally substituted by one or more radicals $R^{13}$, wherein one or more non-adjacent $CH_2$ groups are optionally replaced by $R^{13}C=CR^{13}$, $C\equiv C$, $Si(R^{13})_2$, $Ge(R^{13})_2$, $Sn(R^{13})_2$, C=O, C=S, C=Se, $C=NR^{13}$, $P(=O)(R^3)$, SO, $SO_2$, $NR^{13}$, O, S, or $CONR^{13}$, and wherein one or more H atoms are optionally replaced by D, F, Cl, Br, I, CN, $NO_2$, an aromatic or heteroaromatic ring system having 5 to 60 aromatic ring atoms optionally substituted by one or more radicals $R^{13}$, an aryloxy or heteroaryloxy group having 5 to 60 aromatic ring atoms optionally substituted by one or more radicals $R^{13}$, or a combination of these systems;

$Ar^1$ is, identically or differently on each occurrence, an aromatic or heteroaromatic ring system having 5 to 30 aromatic ring atoms optionally substituted by one or more radicals $R^{13}$; wherein two radicals $Ar^1$ bonded to the same nitrogen, phosphorus, silicon or boron atom are optionally linked to one another by a single bond or a bridge selected from the group consisting of $B(R^{13})$, $C(R^{13})_2$, $Si(R^{13})_2$, C=O, $C=NR^{13}$, $C=C(R^{13})_2$, O, S, S=O, $SO_2$, $N(R^{13})$, $P(R^{13})$, and $P(=O)R^{13}$; and $R^{13}$ is, identically or differently on each occurrence, H, D, or an aliphatic, aromatic, and/or heteroaromatic hydrocarbon radical having 1 to 20 C atoms, wherein one or more H atoms are optionally replaced by D or F; and wherein two or more adjacent substituents $R^{13}$ optionally define a mono- or polycyclic, aliphatic or aromatic ring system.

2. The compound of claim 1, wherein said compound is selected from the group consisting of formulae (4), (5), and (6):

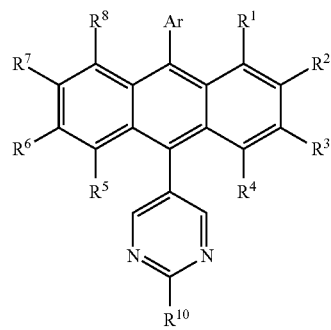

formula (4)

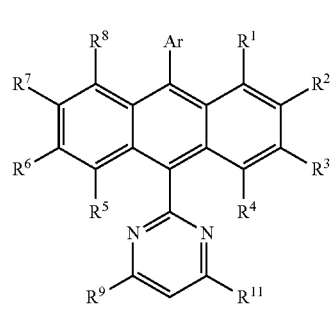

formula (5)

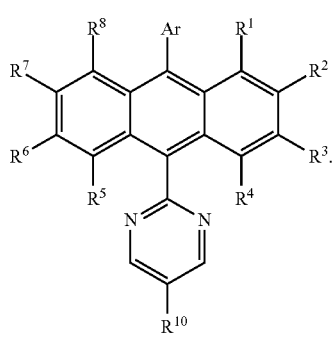

formula (6)

3. The compound of claim 2, wherein said compound is selected from the group consisting of formulae (4a), (5a), and (6a):

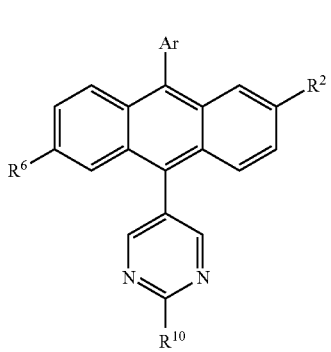

formula (4a)

-continued formula (5a)
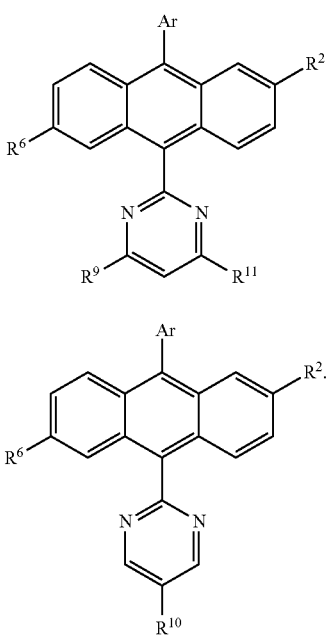

formula (6a)

formula 9a
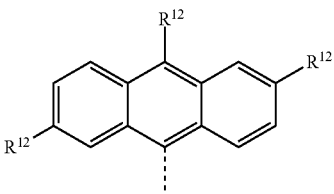

formula 16a
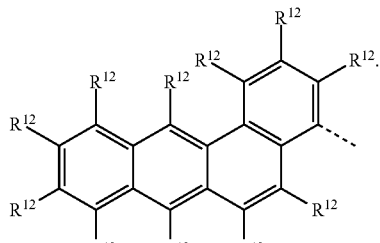

formula (26a)
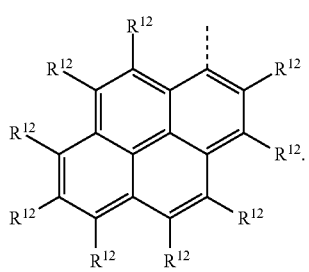

4. The compound of claim 1, wherein Ar is selected from the group consisting of formulae (9a), (10a), (12a), (14a), and (16a)

formula (10a)
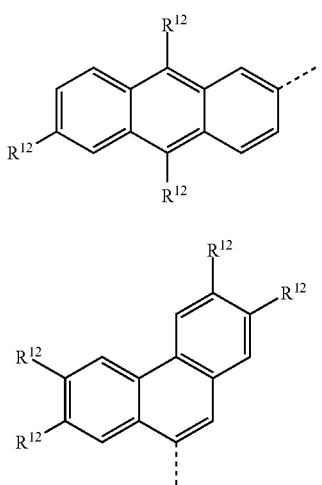

formula (12a)

formula (14a)
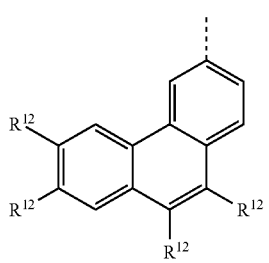

5. The compound of claim 1, wherein the radicals $R^1$ to $R^{12}$ are, identically or differently on each occurrence, selected from the group consisting of H, D, F, $N(Ar^1)_2$, $C(=O)Ar^1$, $P(=O)(Ar^1)_2$, $S(=O)Ar^1$, $S(=O)_2Ar^1$, CN, $Si(R^{13})_3$, a straight-chain alkyl group having 1 to 10 C atoms, and a branched or cyclic alkyl group having 3 to 10 C atoms, each of which is optionally substituted by one or more radicals $R^{13}$, wherein one or more non-adjacent $CH_2$ groups are optionally replaced by $R^{13}C=CR^{13}$, and wherein one or more H atoms are optionally replaced by D, F, or an aromatic or heteroaromatic ring system having 5 to 30 aromatic ring atoms optionally substituted by one or more radicals $R^{13}$.

6. The compound of claim 1, wherein the radicals $R^9$, $R^{10}$ and $R^{11}$ are, identically or differently on each occurrence, H or an aromatic or heteroaromatic ring system having 5 to 24 aromatic ring atoms optionally substituted by one or more radicals $R^{13}$.

7. An electronic device comprising at least one compound of claim 1.

8. The electronic device of claim 7, wherein said electronic device is selected from the group consisting of organic electroluminescent devices, organic integrated circuits, organic field-effect transistors, organic thin-film transistors, organic light-emitting transistors, organic solar cells, organic dye-sensitised solar cells, organic optical detectors, organic photoreceptors, organic field-quench devices, light-emitting electrochemical cells, organic laser diodes, and organic plasmon emitting devices.

9. The electronic device of claim 8, wherein said compound is employed in an electron-transport layer, and/or in an electron-injection layer, and/or in a hole-blocking layer, and/or as matrix material for fluorescent emitters in an emitting layer.

10. The electronic device of claim 9, wherein said compound is employed in an electron-transport layer or in an electron-injection layer in a mixture with a further electron-transport or electron-injection material.

11. A mixture comprising at least one compound of claim 1 and at least one organic alkali-metal compound.

12. A formulation comprising at least one compound of claim 1 and at least one solvent.

13. The compound of claim 1, wherein Ar is selected from one of formulae (12) to (19).

14. A process for preparing the compound of claim 1, comprising reacting an anthracene derivative substituted by a boronic acid group or a boronic acid ester group with a pyrimidine derivative substituted by a reactive leaving group.

15. The electronic device of claim 7, wherein said electronic device is an electroluminescent device.

16. The electronic device of claim 10, wherein said further electron-transport or electron-injection material comprises an organic alkali-metal compound.

17. A compound of formula (4a), formula (5a), or formula (6a),

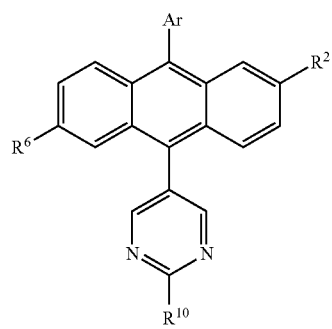

formula (4a)

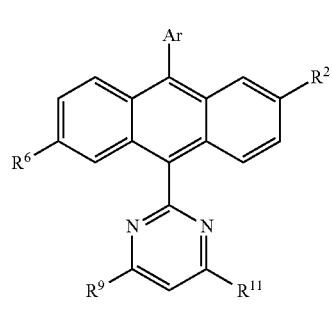

formula (5a)

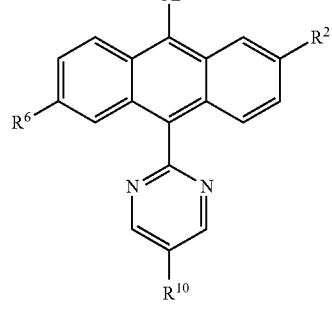

formula (6a)

wherein the dashed bond indicates the bond to the anthracene;

Ar is selected from one group of formulae (9) to (25)

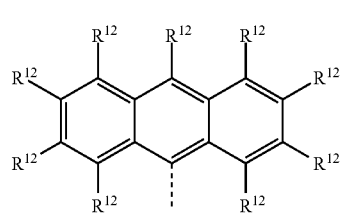

formula 9

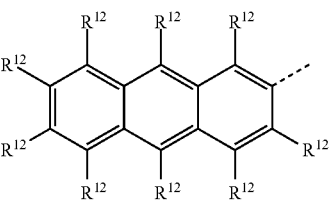

formula (10)

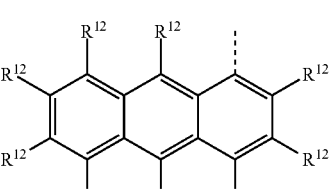

formula (11)

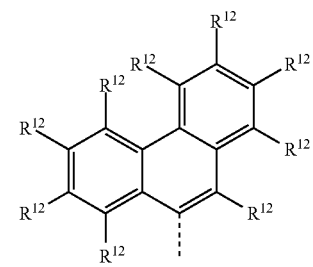

formula (12)

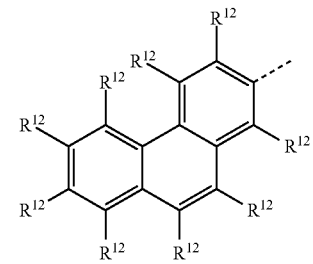

formula (13)

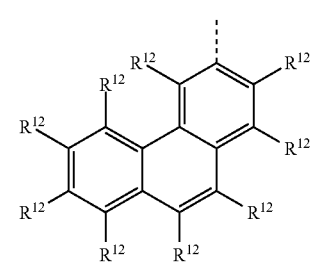

formula (14)

-continued formula (15)
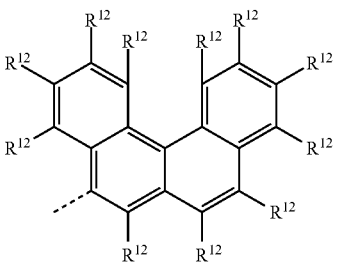

formula (16)
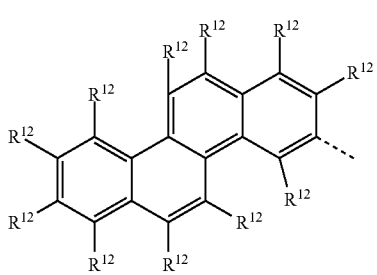

formula (17)
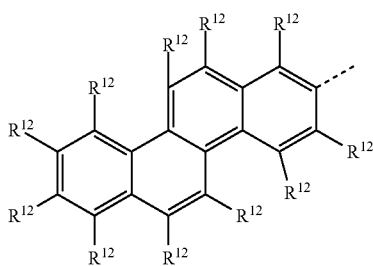

formula (18)
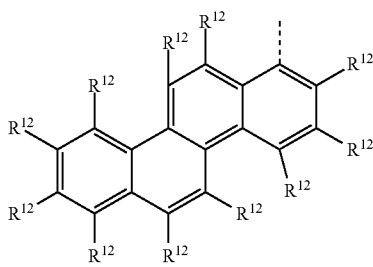

formula (19)
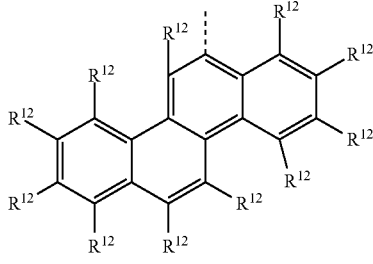

formula (20)
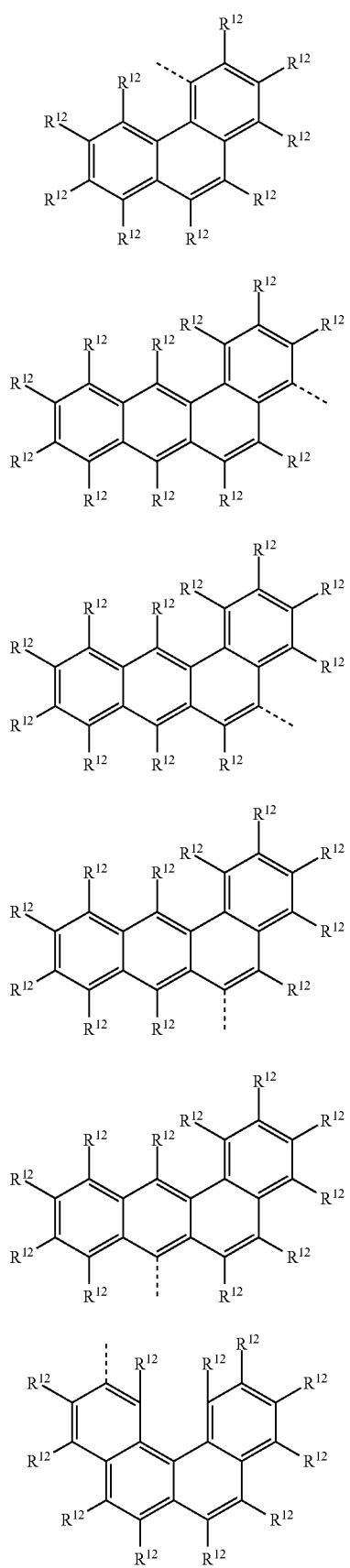

formula (21)

formula (22)

formula (23)

formula (24)

formula (25)

wherein the dashed bond is the position of the link to the anthracene of the compound of formula (1);

$R^1$, $R^2$, $R^3$, $R^4$, $R^5$, $R^6$, $R^7$, $R^8$, $R^9$, $R^{10}$, $R^{11}$, and $R^{12}$ are, identically or differently on each occurrence, H, D, F, $N(Ar^1)_2$, $C(=O)Ar^1$, $P(=O)(Ar^1)_2$, $S(=O)Ar^1$, $S(=O)_2Ar^1$, CN, $Si(R^{13})_3$, a straight-chain alkyl group having 1 to 10 C atoms, and a branched or cyclic alkyl group having 3 to 10 C atoms, each of which is optionally substituted by one or more radicals $R^{13}$, wherein one or more non-adjacent $CH_2$ groups are optionally replaced by $R^{13}C=CR^{13}$, and wherein one or more H atoms are optionally replaced by D, F or an aromatic or heteroaromatic ring system having 5 to 60 aromatic ring atoms optionally substituted by one or more radicals $R^{13}$, an aryloxy or heteroaryloxy group having 5 to 30 aromatic ring atoms optionally substituted by one or more radicals $R^{13}$;

$Ar^1$ is, identically or differently on each occurrence, an aromatic or heteroaromatic ring system having 5 to 30 aromatic ring atoms optionally substituted by one or more radicals $R^{13}$; wherein two radicals $Ar^1$ bonded to the same nitrogen, phosphorus, silicon or boron atom are optionally linked to one another by a single bond or a bridge selected from the group consisting of $B(R^{13})$, $C(R^{13})_2$, $Si(R^{13})_2$, $C=O$, $C=NR^{13}$, $C=C(R^{13})_2$, $O$, $S$, $S=O$, $SO_2$, $N(R^{13})$, $P(R^{13})$, and $P(=O)R^{13}$; and $R^{13}$ is, identically or differently on each occurrence, 1H, D, or an aliphatic, aromatic, and/or heteroaromatic hydrocarbon radical having 1 to 20 C atoms, wherein one or more H atoms are optionally replaced by D or F; and wherein two or more adjacent substituents $R^{13}$ optionally define a mono- or polycyclic, aliphatic or aromatic ring system.

18. The compound of claim 17, wherein the radicals $R^9$, $R^{10}$ and $R^{11}$ are, identically or differently on each occurrence, H or an aromatic or heteroaromatic ring system having 5 to 24 aromatic ring atoms optionally substituted by one or more radicals $R^{13}$.

19. An electronic device comprising at least one compound of claim 18, wherein said electronic device is selected from the group consisting of organic electroluminescent devices, organic integrated circuits, organic field-effect transistors, organic thin-film transistors, organic light-emitting transistors, organic solar cells, organic dye-sensitised solar cells, organic optical detectors, organic photoreceptors, organic field-quench devices, light-emitting electrochemical cells, organic laser diodes, and organic plasmon emitting devices, and wherein said at least one compound is included in an electron-transport layer, an electron-injection layer, in a hole-blocking layer, and/or as a matrix material for fluorescent emitters in an emitting layer.

20. The electronic device of claim 19, wherein the at least one compound is present in an electron-transport layer or in an electron-injection layer with a another electron-transport or electron-injection material, and the electronic device is an organo electroluminescent device.

21. The compound of claim 17, wherein Ar is selected from the group consisting of formulae (9a), (10a), (12a), (14a), and (16a)

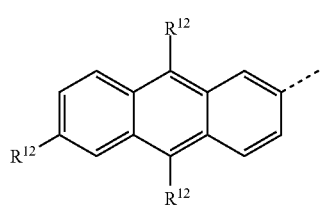

formula (10a)

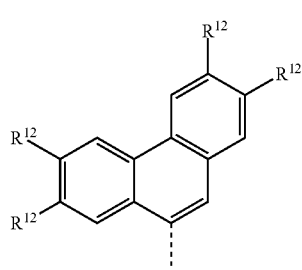

formula (12a)

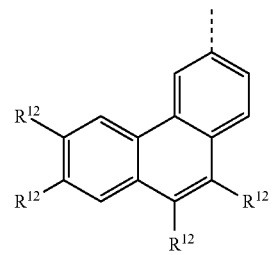

formula (14a)

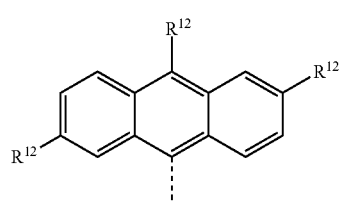

formula 9a

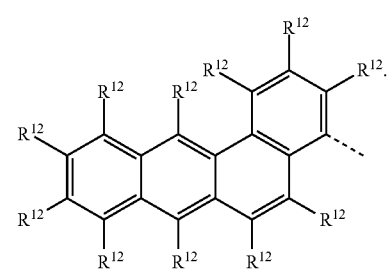

formula 16a

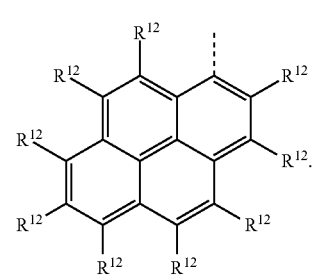

formula (26a)

22. A compound of formula (1)

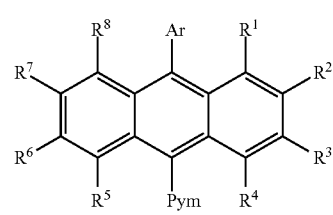

formula (1)

wherein:
Pym is selected from the group consisting of formula (2) and formula (3),

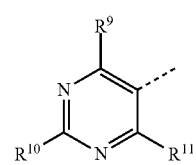

formula (2)

-continued

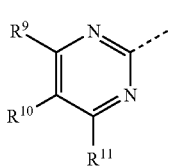

formula (3)

wherein the dashed bond indicates the bond to the anthracene;

Ar is selected from the group consisting of formulae (9a), (10a), and (16a)

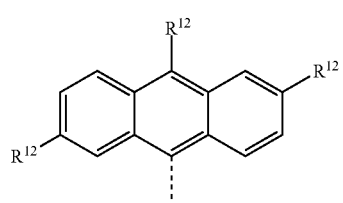

formula 9a

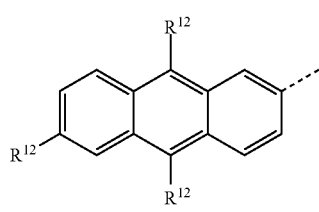

formula 10a

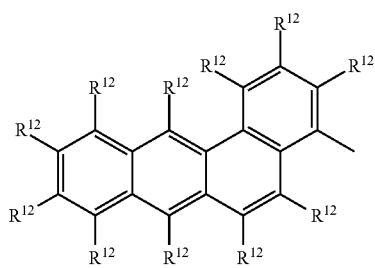

formula 16a wherein the dashed bond is the position of the link to the anthracene of the compound of formula (1);

$R^1$, $R^2$, $R^3$, $R^4$, $R^5$, $R^6$, $R^7$, $R^8$, $R^9$, $R^{10}$, $R^{11}$, and $R^{12}$ are, identically or differently on each occurrence, H, D, F, Cl, Br, I, CHO, $N(R^{13})_2$, $N(Ar^1)_2$, $B(Ar^1)_2$, $Si(R^{13})_2$, $Si(Ar^1)_2$, $C(=O)Ar^1$, $P(=O)(Ar^1)_2$, $S(=O)Ar^1$, $S(=O)_2Ar^1$, $CR^{13}=CR^{13}Ar^1$, CN, $NO_2$, $Si(R^{13})_3$, $B(OR^{13})_2$, $B(R^{13})_2$, $B(N(R^{13})_2)_2$, $OSO_2R^{13}$, a straight-chain alkyl, alkenyl, alkynyl, alkoxy or thioalkoxy group having 1 to 40 C atoms, or a branched or cyclic alkyl, alkenyl, alkynyl, alkoxy or thioalkoxy group having 3 to 40 C atoms, each of which is optionally substituted by one or more radicals $R^{13}$, wherein one or more non-adjacent $CH_2$ groups are optionally replaced by $R^{13}C=CR^{13}$, C≡C, $Si(R^{13})_2$, $Ge(R^{13})_2$, $Sn(R^{13})_2$, C=O, C=S, C=Se, $C=NR^{13}$, $P(=O)(R^{13})$, SO, $SO_2$, $NR^{13}$, O, S, or $CONR^{13}$, and wherein one or more H atoms are optionally replaced by D, F, Cl, Br, I, CN, $NO_2$, an aromatic or heteroaromatic ring system having 5 to 60 aromatic ring atoms optionally substituted by one or more radicals $R^{13}$, an aryloxy or heteroaryloxy group having 5 to 60 aromatic ring atoms optionally substituted by one or more radicals $R^{13}$, or a combination of these systems; and wherein two or more adjacent substituents $R^1$ to $R^{12}$ optionally define a mono- or polycyclic, aliphatic or aromatic ring system;

$Ar^1$ is, identically or differently on each occurrence, an aromatic or heteroaromatic ring system having 5 to 30 aromatic ring atoms optionally substituted by one or more radicals $R^{13}$; wherein two radicals $Ar^1$ bonded to the same nitrogen, phosphorus, silicon or boron atom are optionally linked to one another by a single bond or a bridge selected from the group consisting of $B(R^{13})$, $C(R^{13})_2$, $Si(R^{13})_2$, C=O, $C=NR^{13}$, $C=C(R^{13})_2$, O, S, S=O, $SO_2$, $N(R^{13})$, $P(R^{13})$, and $P(=O)R^{13}$; and $R^{13}$ is, identically or differently on each occurrence, H, D, or an aliphatic, aromatic, and/or heteroaromatic hydrocarbon radical having 1 to 20 C atoms, wherein one or more H atoms are optionally replaced by D or F; and wherein two or more adjacent substituents $R^{13}$ optionally define a mono- or polycyclic, aliphatic or aromatic ring system.

* * * * *